US006372436B1

(12) United States Patent
Pouzyrev et al.

(10) Patent No.: US 6,372,436 B1
(45) Date of Patent: Apr. 16, 2002

(54) METHOD FOR CONSTRUCTION OF CDNA LIBRARIES ENRICHED IN CLONES CORRESPONDING TO RARE MRNA

(75) Inventors: Anatoli Timofeyevich Pouzyrev; Donald Lee Riddle, both of Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/662,235

(22) Filed: Sep. 14, 2000

(51) Int. Cl.[7] ............................ C12Q 1/68; C12P 19/34; C07H 21/02; C07H 21/04; C12N 15/00
(52) U.S. Cl. ..................... 435/6; 435/91.1; 536/23.1; 536/24.3; 935/76; 935/77; 935/78
(58) Field of Search ................ 435/6, 91.2; 536/23.1, 536/24.3; 935/76, 77, 78

(56) References Cited

U.S. PATENT DOCUMENTS

| | | | |
|---|---|---|---|
| 5,482,845 A | | 1/1996 | Soares et al. |
| 5,637,685 A | | 6/1997 | Soares et al. |
| 5,702,898 A | | 12/1997 | Bonaldo et al. |
| 5,830,662 A | * | 11/1998 | Soares et al. .................. 435/6 |
| 5,846,721 A | | 12/1998 | Soares et al. |
| 6,060,240 A | * | 5/2000 | Kamb et al. ................... 435/6 |
| 6,060,245 A | * | 5/2000 | Sorge et al. .................... 435/6 |
| 6,218,123 B1 | * | 4/2001 | Nehls et al. .................... 435/6 |

OTHER PUBLICATIONS

Bonaldo, M. F., Lennon, G., and Soares, M. B. (1996). Normalization and subtraction: two approaches to facilitate gene discovery. *Genome Research* 6, 791–806.

Ko, M. S. H. (1990). An equalized cDNA library by reassociation of short double–stranded cDNAs. *Nucleic Acids Res.* 5705–5711.

Patanjali, S. R., Parimoo, S. & Weissman, S. M. (1991). Construction of a uniform–abundance (normalized) cDNA library. *Proc. Natl. Acad. Sci. USA* 88, 1943–1947.

Soares, M. B., Bonaldo, M. F., Jelene, P., Su, L., Lawton, L., & Efstratiadis, A. (1994). Construction and characterization of a normalized cDNA library. *Proc. Natl. Acad. Sci. USA* 91, 9228–9232.

Puzyrev, A. T., Chroniary K., & Moschonas, N. K. (1995). Normalized cDNA library from human erythroleukemia cells. *Mol. Biol. Engl. Tr.* 29, 58–61.

Puzyrev, A. T., Il'ichev, A. A., Petrenko, V. A. (1990). A method for equalizating concentrations of dsDNAs in a mixture. In *Abstracts of the 1st Conference on Human Genome* (Moscow), pp. 91–92, in Russian.

Sasaki, Y.F., Ayusawa, D., & Oishi, M. (1994). Construction of a normalized cDNA library by introduction of a semi–solid mRNA–cDNA hybridization system. *Nucleic Acids Res.* 22, 987–992.

Lisitsyn et al., Science 259: 946–951 (1993).*

Hubank et al., Nucleic Acids Research 22(25): 5640–5648 (1994).*

* cited by examiner

*Primary Examiner*—Ethan C. Whisenant
(74) *Attorney, Agent, or Firm*—John P. White; Cooper & Dunham LLP

(57) ABSTRACT

The present invention provides for a method for producing a cDNA library enriched for rare cDNAs and reduced in abundant cDNAs which comprises: (a) obtaining a pool of linear double-stranded cDNAs; (b) cloning a first portion of the pool of cDNAs into a first vector to create a first cDNA library; (c) cloning a second portion of the pool of cDNAs into a second vector to create a second cDNA library; (d) producing single-stranded linear cDNA inserts (target cDNA) from the first cDNA library; (e) producing single-stranded circles (target cDNA) from the second cDNA library; (f) producing a pool of abundant linear cDNAs (driver cDNA) from the first and the second DNA libraries; (g) hybridizing the linear cDNA inserts from step (d) or the single-stranded circles from step (e) with an excess amount of the abundant cDNA pool produced from the second cDNA library or the first cDNA library, respectively, from step (f) under hybridization conditions to produce duplexes, and (h) isolating single-stranded linear cDNA inserts or single-stranded circles which remain after the hybridization of step (g), thereby producing cDNA or a cDNA library enriched for rare cDNAs and reduced in abundant cDNAs.

15 Claims, 7 Drawing Sheets

Preparation of cDNA libraries in lambda gt11 and lambda ZapII

FIGURE 2  Preparation of abundant cDNA pool

FIGURE 3 Subtraction of abundant cDNAs from unnormalized cDNAs (method 1)

Comparative analysis of unnormalized and rare cDNAs from *C. elegans* dauer larvae by Southern hybridization with 5 probes daf-7   daf-1   daf-4   ama-1   Hsp90

| 2.6 | 3.3 | 6 | 11 | 273 | Molecules per 100,000 molecules in unnormalized cDNA |
|-----|-----|---|----|----|------|
| 245 | 186 | 234 | 20 | 91 | Molecules per 100,000 molecules in rare cDNA |

Comparative analysis of unnormalized and rare cDNAs from *C. elegans* dauer larva by Southern hybridization with 5 probes daf-7    daf-1    daf-4    ama-1    Hsp90

| 2.6 | 3.3 | 6 | 11 | 273 | Molecules per 100,000 molecules in unnormalized cDNA |
|---|---|---|---|---|---|
| 17 | 10 | 22 | 11 | 8 | Molecules per 100,000 molecules in rare cDNA |

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 1
ctcctggagc ccgtcagtat              20

-continued

```
<210> SEQ ID NO 2
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 2
gtaatggtag cgaccggcgc                                              20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 3
ggagcccgtc agtatcggcg                                              20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 4
gtagcgaccg gcgctcagct                                              20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 5
tcgaggtcga cggtatcgat                                              20

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 6
ccgctctaga actagtggat c                                            21
```

METHOD FOR CONSTRUCTION OF CDNA LIBRARIES ENRICHED IN CLONES CORRESPONDING TO RARE MRNA

The invention disclosed herein was made with Government support under Grant Nos. RO1 AG12689 and RO1 GM60515 from the U.S. Department of Health and Human Services, National Institutes of Health. Accordingly, the U.S. Government has certain rights in this invention.

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

BACKGROUND OF THE INVENTION

Sequencing of the ends of a large number of cDNA clones (ESTs, expressed sequence tags) is a parallel effort to genome sequencing. Genes predicted in genomic sequences are verified only if they are expressed in the form of RNA. These RNAs are represented as clones in cDNA libraries. Accelerating the discovery of new ESTs may greatly expedite the identification and cloning of human disease genes. Many ESTs are not full length; however, they provide important information for identification of expressed genes, verification of the exon-intron boundaries predicted from genome sequences, and detection of alternative splicing.

The copy number of mRNAs in a eukaryotic cell can differ by factors of thousands (Lewin 1994). The problem of detecting genes expressed at low levels is illustrated in the simple animal model *C. elegans*, which has a small genome of $10^8$ base pairs predicted to encode only 19,000 genes (Thierry-Mieg et al. 1999). Forty thousand (40,000) cDNA clones from a large normalized cDNA library of *C. elegans* were sequenced to detect the first 7,400 expressed genes. The average rate of detecting genes was 5.4 clones per gene (The *C. elegans* Sequencing Consortium 1998). Twenty-five thousand (25,000) clones were sequenced to detect the next 1,700 expressed genes, an average rate of 14.7 clones per gene (Thierry-Mieg et al. 1999, Kohara et al. 1999).

To detect genes expressed at lower levels than the genes already found, there is a need for better cDNA libraries. With the dramatically accelerated sequencing of the human genome, high priority should be placed on developing technology for finding rare ESTs. This raises the question of how to search for recombinant clones corresponding to rare mRNA species. Clearly, identification of such clones requires screening of large (complex) cDNA libraries. For the purpose of gene discovery, it would be attractive to construct cDNA libraries containing nearly equal amounts of cDNA from each expressed gene. Contents of different double-stranded DNAs have been equalized from mixtures of abundant and rare restriction fragments as a model system (Puzyrev et al. 1990). Since reassociation kinetics of denatured double-stranded DNAs obey the second-order equation $V_i = K_i (\text{ssDNA}_i)^2$, the concentrations of different unhybridized DNA molecules can become nearly equal after partial reassociation. The unhybridized single-stranded DNAs can be separated from hybridized double-stranded molecules by hydroxyapatite chromatography and can be cloned after conversion into double-stranded DNA. This principle has been used previously for preparation of normalized cDNA libraries.

Methods to Normalize cDNA Libraries

Five groups have developed methods to normalize cDNA libraries based on the kinetic approach (Ko, 1990; Patanjali et al., 1991; Sasaki et al., 1994; Soares et al., 1994; Puzyrev et al., 1995; Soares et al., 1996). Ko (1990) described the construction of a normalized cDNA library by a method involving: (a) ligation of a linker-primer adaptor to cDNAs; (b) three rounds of PCR amplification, denaturation and partial reassociation; (c) separation of single-stranded cDNAs from double-stranded cDNAs by hydroxyapatite chromatography; (d) conversion of single-stranded cDNAs into double-stranded cDNAs; (e) digestion of the end product using a site present in the linker-primer sequence; and (f) ligation into a vector for cloning. Colony hybridization with eight probes showed a reduction in "abundance variation" after three cycles of normalization. The concentration of some abundant clones decreased up to 34-fold and the concentration of some rare clones increased up to 2.6-fold. However, for some abundant clones the extent of normalization was low, and the concentration of one abundant clone even increased in the normalized library.

Patanjali et al. (1991) constructed a normalized cDNA library by a method similar to that of Ko, involving: (a) synthesis of double-stranded cDNAs by random priming and cloning them in a vector; (b) amplification of the cloned cDNAs by PCR; (c) denaturation and partial reassociation; (d) separation of single-stranded cDNAs from double-stranded cDNAs by hydroxyapatite chromatography; (e) amplification of single-stranded cDNAs by PCR; (f) ligating the products into a vector for cloning. Analysis with 10 probes showed an extreme decrease of concentration for a very abundantly expressed ribosomal gene (30% in the unnormalized library, and 2,500 times less in the normalized library), and the concentration of some rare clones increased up to 3-fold. As in Ko's method, the extent of normalization was lower than expected for some clones.

Puzyrev et al. (1995) reported the construction of a normalized cDNA library by a similar method, which involved: (a) amplification of cloned cDNAs by PCR; (b) denaturation and partial reassociation of amplified cDNAs in the presence of excess "competitors"—sequences common to all cDNAs; (c) separation of single-stranded cDNAs from double-stranded cDNAs by hydroxyapatite chromatography; (d) amplification of single-stranded cDNAs by PCR; and (e) cloning these cDNAs into lambda gt11. Analysis with ten probes showed that abundant clones were reduced 3–20 fold, but the less abundant clones tested were not greatly enriched.

Sasaki et al. (1994) constructed a normalized cDNA library by a procedure which involved: (a) synthesis of first-rate cDNA; (b) binding the cDNA to a matrix; (c) sequential cycles of hybridizing the matrix-bound cDNA with a corresponding whole mRNA population and eluting unhybridized mRNA; and (e) constructing a normalized cDNA library with use of mRNA eluted in step (c). Analysis with 7 probes showed a 100-fold decrease in concentration for an abundant β-globin clone, and an increase up to 6-fold for four rare clones.

Soares et al. (1994) described the construction of a normalized cDNA library from human infant brain by a method involving: (a) construction of a cDNA library in a vector capable of being converted to single-stranded circles, and capable of producing strands complementary to the single-stranded circles; (b) converting the cDNA library to single-stranded circles; (c) generating strands complementary to the single-stranded circles; (d) hybridizing the single-stranded circles converted in step (b) with complementary strands of step (c) to produce partial duplexes; (e) separating the unhybridized single-stranded circles from the hybridized circles by hydroxyapatite chromatography; (f) conversion of the unhybridized single-stranded circles into partial duplexes; and (g) electroporation into E. coli. Normalization was achieved with this method for most cDNA species examined. The concentration of "rare cDNAs" were increased in normalized libraries by 2–30 times; however, the concentrations of some abundant cDNAs were reduced only 3-fold.

Bonaldo et al. (1996) reported the construction of cDNA libraries from human, mouse, and rat by normalization and subtraction. Several methods were described. For example, to avoid or reduce continued isolation of known clones, subtractive hybridization was applied to reduce the representation of previously arrayed and sequenced clones from normalized libraries. Another method to improve normalization used RNA synthesized from abundant cDNAs to hybridize with single-stranded circles from the starting library. The subtractive method involved: (a) construction of a cDNA library using a vector that permits both transcription of the cDNA inserts and conversion of the cDNA library to single-stranded circles; (b) transcription of the cDNA inserts in vitro; (c) purification of the single-stranded circles by hydroxyapatite chromatography; (d) in the presence of blocking oligonucleotides, hybridizing the single-stranded circles prepared in step (c) at an appropriate $C_o t$ with complementary RNAs from step (b) to produce partial duplexes; (e) separating the partial duplexes from the single-stranded circles by HAP-chromatography; (f) converting the partial duplexes to complete double-stranded DNA circles and electroporating them into E. coli to create a mini-library enriched for abundant cDNAs; (g) transcribing the double-stranded plasmid mini-library from (f); (h) hybridizing the single-stranded circles purified in step (c) with abundant RNAs from step (g) at an appropriate $C_o t$ (i), separating unhybridized single-stranded circles from step (h) by HAP-chromatography; and (j) converting single-stranded circles from step (i) into double-stranded circles and electroporating them into E. coli to generate a subtractive cDNA library.

SUMMARY OF THE INVENTION

The present invention provides for a method for producing a cDNA library enriched for rare cDNAs and reduced in abundant cDNAs which comprises: (a) obtaining a pool of linear double-stranded cDNAs; (b) cloning a first portion of the pool of cDNAs into a first vector to create a first cDNA library; (c) cloning a second portion of the pool of cDNAs into a second vector to create a second cDNA library; (d) producing single-stranded linear cDNA inserts (target cDNA) from the first cDNA library; (e) producing single-stranded circles (target cDNA) from the second cDNA library; (f) producing a pool of abundant linear cDNAs (driver cDNA) from the first and the second DNA libraries by the following steps: (i) amplifying the cDNA inserts from the first and the second libraries by polymerase chain reaction using two pairs of appropriate primers which specifically hybridize with the first and second vectors, respectively; (ii) removing DNA sequences common to all of the amplified products from step (i); (iii) denaturing the amplified products from step (ii); (iv) partially reassociating the denatured products from step (iii) in a hybridization mixture under appropriate hybridization conditions so as to produce duplexes of abundant cDNAs, and (v) removing unreassociated cDNAs from step (iv), thereby producing the pools of abundant linear cDNAs from the first and the second cDNA libraries; (g) hybridizing the linear cDNA inserts from step (d) or the single-stranded circles from step (e) with an excess amount of the abundant cDNA pool produced from the second cDNA library or the first cDNA library, respectively, from step (v) under hybridization conditions to produce duplexes, and (h) isolating single-stranded linear cDNA inserts or single-stranded circles which remain after the hybridization of step (g), thereby producing cDNA or a cDNA library enriched for rare cDNAs and reduced in abundant cDNAs.

BRIEF DESCRIPTION OF THE FIGURES

FIG. 7A—Southern hybridization of $^{32}$p-labeled probes corresponding to 20 random clones from the rare cDNA library with the unnormalized (left lane) and rare (right lane) cDNA inserts obtained by digestion of the two libraries with EcoRI. Hybridization signals were quantified with a phosphorimager; exposed X-ray films are shown. FIG. 7B—Southern hybridization of three abundant clones from unnormalized cDNA libraries with the unnormalized and rare cDNAs, as in FIG. 7A.

DETAILED DESCRIPTION OF THE INVENTION

Figure 1:
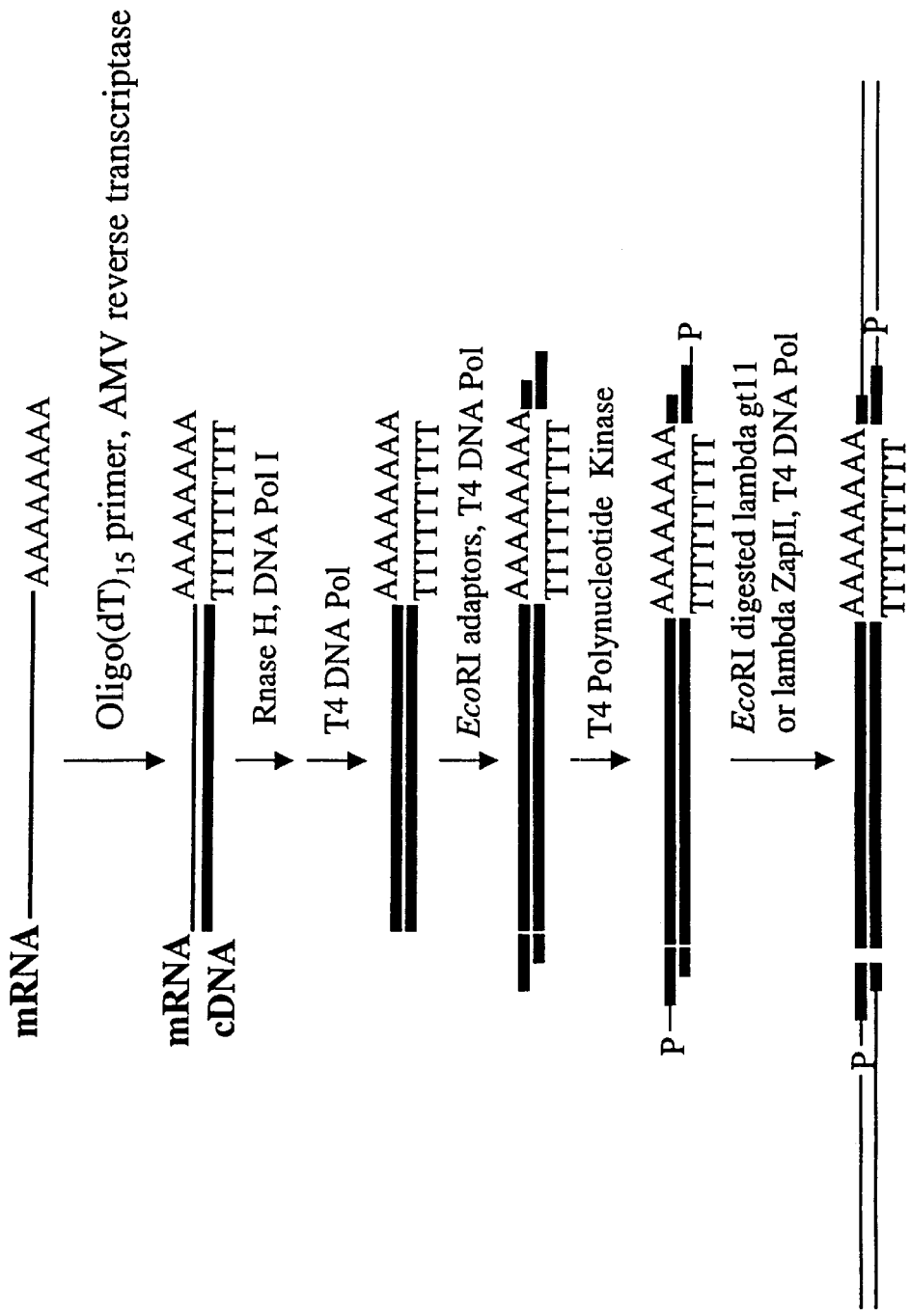
FIG. 1: Making cDNA libraries from C. elegans dauer larvae. The cDNA (synthesized using a Promega kit) was cloned into the EcoRI site of two phage vectors: lambda gt11 and lambda ZapII™.

The present invention provides for a method for producing a cDNA library enriched for rare cDNAs and reduced in abundant cDNAs which comprises: (a) obtaining a pool of linear double-stranded cDNAs; (b) cloning a first portion of the pool of cDNAs into a first vector to create a first cDNA library; (c) cloning a second portion of the pool of cDNAs into a second vector to create a second cDNA library; (d) producing single-stranded linear cDNA inserts (target cDNA) from the first cDNA library; (e) producing single-stranded circles (target cDNA) from the second cDNA library; (f) producing a pool of abundant linear cDNAs (driver cDNA) from the first and the second DNA libraries by the following steps: (i) amplifying the cDNA inserts from the first and the second libraries by polymerase chain reaction using two pairs of appropriate primers which specifically hybridize with the first and second vectors, respectively; (ii) removing DNA sequences common to all of the amplified products from step (i); (iii) denaturing the amplified products from step (ii); (iv) partially reassociating the denatured products from step (iii) in a hybridization mixture under appropriate hybridization conditions so as to produce duplexes of abundant cDNAs, and (v) removing unreassociated cDNAs from step (iv), thereby producing the pools of abundant linear cDNAs from the first and the second cDNA libraries; (g) hybridizing the linear cDNA inserts from step (d) or the single-stranded circles from step (e) with an excess amount of the abundant cDNA pool produced from the second cDNA library or the first cDNA library, respectively, from step (v) under hybridization conditions to produce duplexes, and (h) isolating single-stranded linear cDNA inserts or single-stranded circles which remain after the hybridization of step (g), thereby producing cDNA or a cDNA library enriched for rare cDNAs and reduced in abundant cDNAs.

In one embodiment of the invention, removing common sequences in step (f) (ii) is performed by restriction enzyme digestion of the amplified products.

In another embodiment of the invention, isolating the reassociated abundant cDNA duplexes of step (f) (v) is performed by treating the hybridization mixtures of step (f) (iv) with S1 nuclease so as to degrade any single-stranded cDNAs.

In another embodiment of the invention, isolating unreassociated linear cDNAs or single-stranded circles from reassociated cDNA duplexes of step (g) is performed by subjecting the hybridization mixtures to hydroxyapatite column chromatography so as to separate single-stranded cDNAs or single-stranded circles from DNA duplexes.

In another embodiment of the invention, the pool of linear double-stranded cDNAs of step (a) comprises cDNAs produced by reverse transcriptase using mRNA isolated from a biological sample.

In another embodiment, the biological sample is a human biological sample or a non-human biological sample. In another embodiment, the human biological sample is a tissue sample, a blood sample, a saliva sample, an embryonic sample or a tumor biopsy.

In another embodiment, the non-human biological sample is an embryonic sample, a tissue sample, an animal sample or a plant sample.

In one embodiment, the biological sample is derived or obtained from any animal species, any plant species or any bacterial species. For example, the biological sample may be obtained or derived from a human, a mouse, a rat, a dog, a fowl, a reptile, a horse, a bovine, a fish, a primate, a feline, a bacterial cell, a yeast, a fungi, a seed, or a plant.

In one embodiment of the invention, the first vector or the second vector is a phage vector, a phagemid vector, a retroviral vector or a plasmid vector. In one preferred embodiment, the first vector is a lambda gt11 phage vector. In another preferred embodiment, the second vector is a lambda ZapII™ vector.

In another embodiment, the method provided herein further comprises: (a) amplifying the single-stranded linear cDNA inserts in step (h) by polymerase chain reaction using primers specific for the first vector, so as to thereby produce cDNA enriched for rare cDNAs and reduced in abundant cDNAs; (b) electroporating single-stranded circles in step (h) into host cells or converting single-stranded circles in step (h) into double-stranded circles and electroporating them into host cells, so as to thereby produce a cDNA library enriched for rare cDNAs and reduced in abundant cDNAs.

In one embodiment, the hybridization conditions to produce duplexes of step (g) comprise 0.3 M sodium phosphate (pH 7.0) to $C_o$ts 20 to 380.

In a preferred embodiment, the first vector is lambda gt11 and the two primer pairs used for polymerase chain reaction have the following sequences:

(a) 5'-CTCCTGGAGCCCGTCAGTAT-3' (SEQ ID NO:1) and 5'-GTAATGGTAGCGACCGGCGC-3' (SEQ ID NO:2);

(b) 5'-GGAGCCCGTCAGTATCGGCG-3' (SEQ ID NO:3) and 5'-GTAGCGACCGGCGCTCAGCT-3' (SEQ ID NO:4).

In another preferred embodiment, the second vector is lambda ZapII™ and the primers used for polymerase chain reaction have the following sequences:

5'-TCGAGGTCGACGGTATCGAT-3' (SEQ ID NO:5) and

5'-CCGCTCTAGAACTAGTGGATC-3' (SEQ ID NO:6).

In one embodiment, the rare cDNAs produced from the method presented herein are hybridized to microarrayed cDNAs for further analysis.

The present invention provides a new and improved method to facilitate gene discovery that can be used to aid analysis of gene expression in any organism. The products of different genes are present in greatly different amounts within a cell, and when recombinant cDNA libraries are constructed representing these products, the vast majority of clones in the library represent abundant products. Rare clones that typically represent the majority of expressed genes are of equal interest, but they constitute a small minority of the clones in the library. For the purpose of gene discovery, one would ideally construct "normalized" libraries containing equal amounts of cDNA from each expressed gene in order to avoid repeated analysis of the same abundant clones while missing the rare clones. Using the nematode *Caenorhabditis elgans* as a model organism with a sequenced genome (19,000 predicted genes, about 9,100 of which have been detected in cDNA libraries), the method presented herein increases the concentration of clones representing rare products in a cDNA library more than any other previous method. The sequences of 20 random clones from one such library revealed that ten of the clones represented genes not previously detected by the *C. elegans* EST (expressed sequence tag) sequencing project. The present invention will greatly improve the efficiency of gene discovery in animal and plant genome projects by saving time and greatly reducing costs.

This invention provides two new methods based on a kinetic approach to enrich the representation of rare cDNAs in cDNA libraries. Briefly, a cDNA library in a lambda gt11 or lambda ZapII™ vector is used as a template to amplify cDNA inserts by PCR. Common sequences at the ends of amplified cDNAs are removed by EcoRI. The cDNAs are denatured and then reassociated to a $C_ot$ of up to 380. After digestion of unreassociated single-stranded cDNAs with S1 nuclease, the remaining double-stranded cDNAs serve as an abundant cDNA pool. The cDNA library in lambda gt11 is used as a template to amplify cDNA inserts in single-stranded form, and the cDNA library in lambda ZapII™ is used to prepare single-stranded circles with cDNA inserts. In the first method, single-stranded cDNAs are mixed with abundant cDNAs, and the mixture is denatured and partially reassociated. Unreassociated single-stranded cDNAs are separated from reassociated double-stranded cDNAs by hydroxyapatite chromatography and used for preparation of cDNAs enriched in sequences representing rare mRNAs. In the second method, single-stranded cDNA circles are mixed with abundant cDNAs, then denatured and partially reassociated. Unreassociated single-stranded circles are separated from reassociated partial duplexes by hydroxyapatite chromatography and used for preparation of cDNA libraries enriched in clones representing rare mRNAs.

Figure 2:
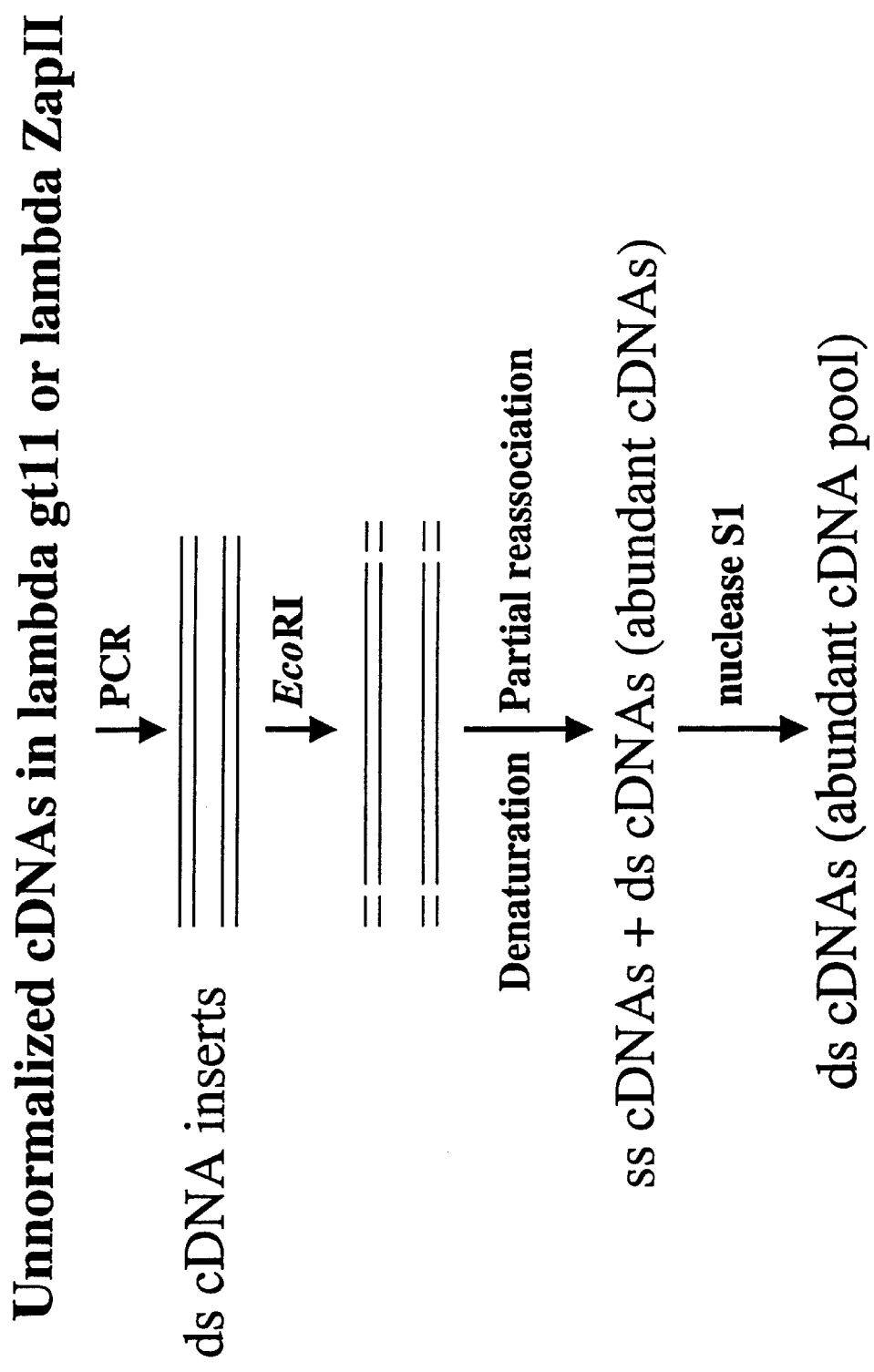
FIG. 2: Preparation of an abundant cDNA pool from cDNAs amplified from lambda ZapII™ or lambda gt11. Up to 200 μg of PCR-amplified cDNA inserts were digested with EcoRI, then denatured and partially reassociated in 0.3 M sodium phosphate. Unreassociated single-stranded cDNAs, as well as single-stranded portions of reassociated cDNAs, were digested by S1 nuclease.
Figure 3:
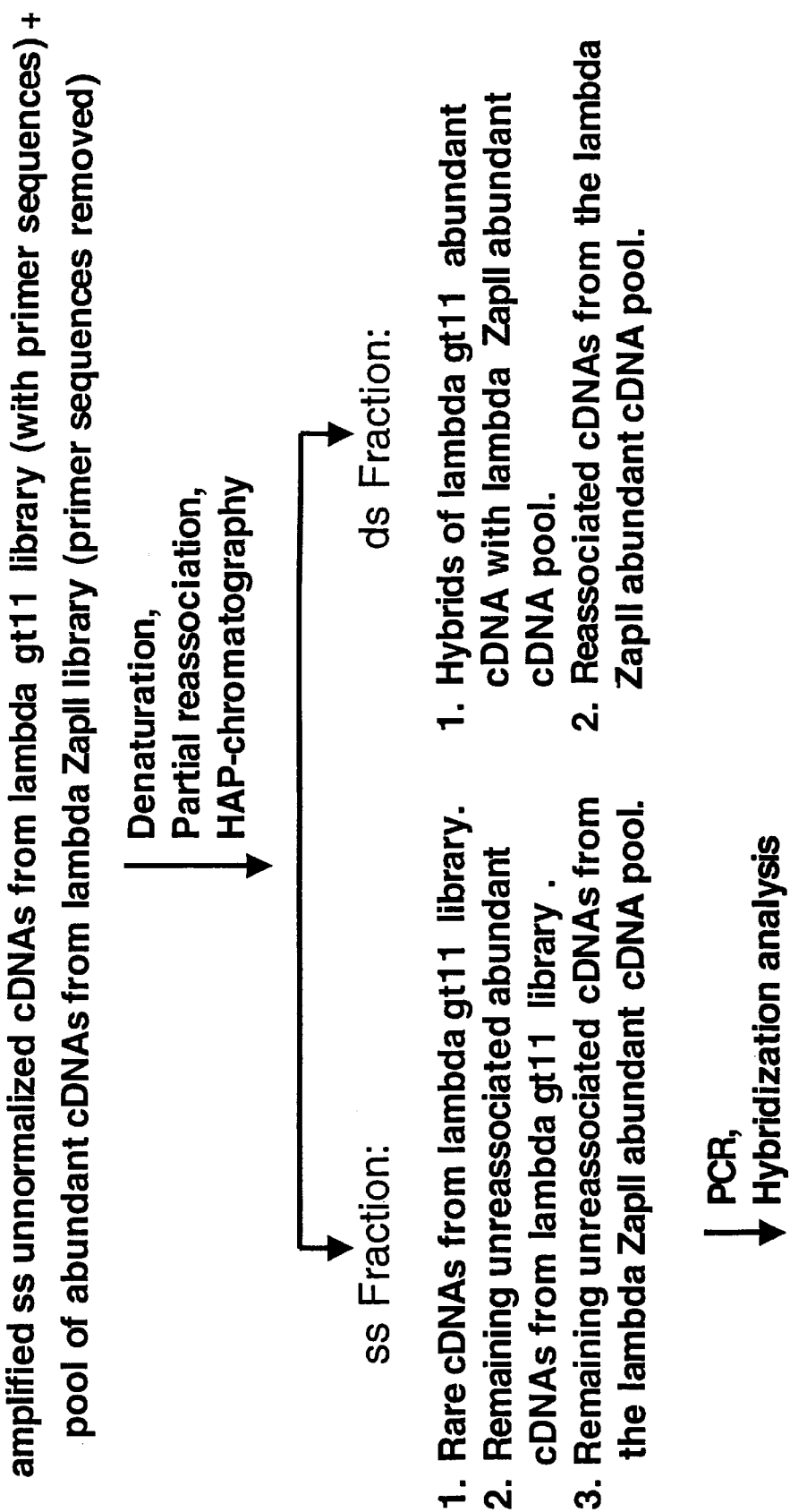
FIG. 3: Subtraction of abundant cDNAs from unnormalized cDNAs (method 1). Unnormalized (target) single-stranded cDNA was mixed with an excess of abundant (driver) cDNA. Partial reassociation was conducted in 0.3 M sodium phosphate. Unreassociated single-stranded molecules were separated from reassociated double-stranded cDNAs by hydroxyapatite chromatography. Single-stranded cDNAs containing primer sequences were converted into the double-stranded form and used for hybridization analysis.
Figure 4:
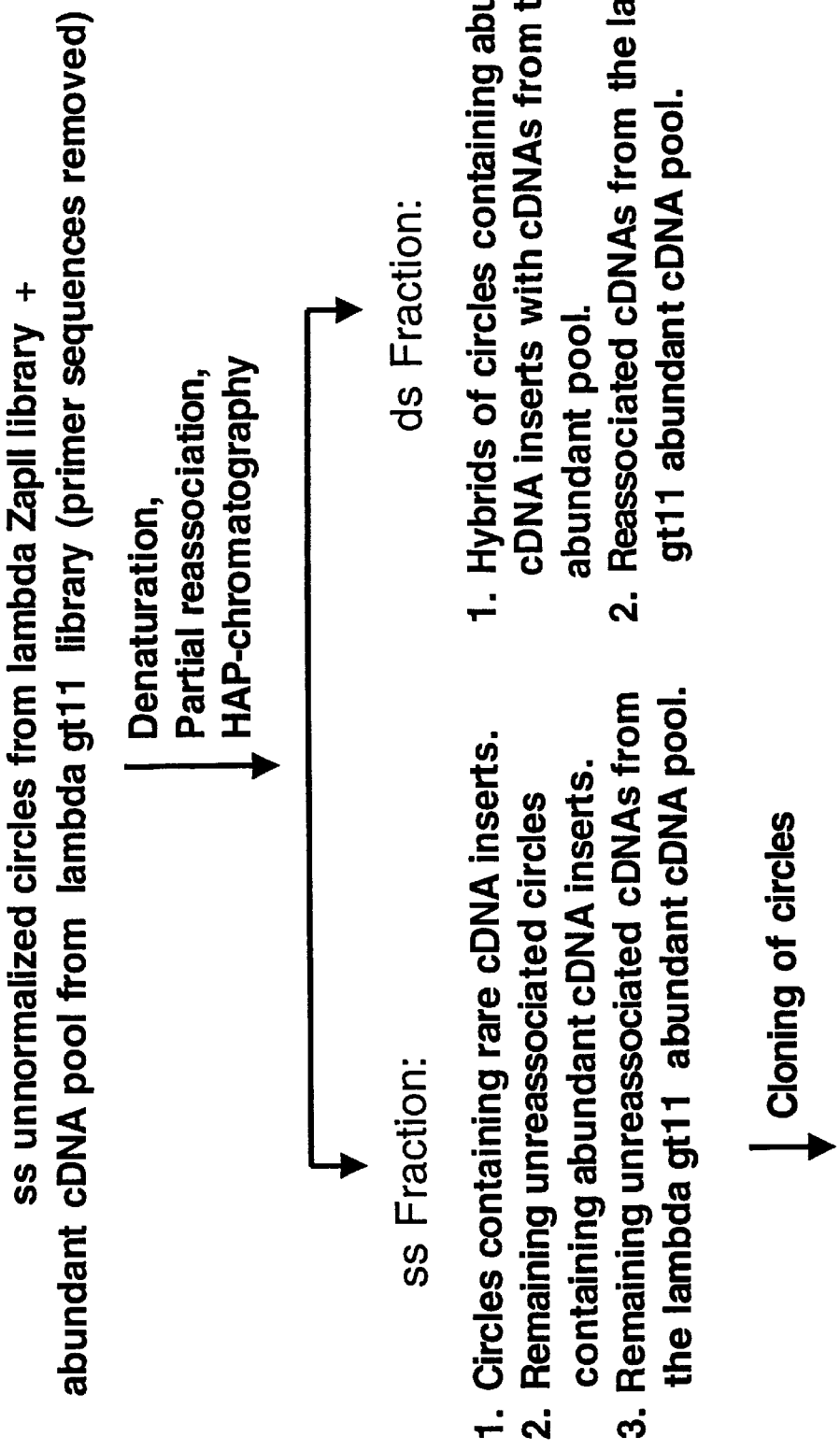
FIG. 4: Subtraction of abundant cDNAs from single-stranded circles containing cDNA inserts (method 2). Unnormalized single-stranded circles (target) were mixed with an excess of abundant (driver) cDNAs, and partially reassociated in 0.3 M sodium phosphate. Remaining single-stranded circles were separated from partial hybrids by hydroxyapatite chromatography, and electroporated into E. coli to be cloned.

This invention provides a simplified and effective method to enrich cDNA libraries for clones representing rare mRNAs. The method consists of: (a) constructing cDNA libraries in two vectors containing the same set of cDNA inserts, wherein the inserts are capable of being amplified by polymerase chain reaction (PCR) with appropriate primers (FIG. 1); (b) generating either single-stranded or double-stranded linear cDNA inserts from cDNA libraries constructed in step (a) by PCR; (c) generating single-stranded circles from one of the two cDNA libraries in (a); (d) digesting the double-stranded cDNA inserts generated in step (b), with EcoRI, to remove common primer sequences, then denaturing and partially reassociating at an appropriate $C_ot$ (FIG. 2); (e) degrading unreassociated cDNA inserts from step (d) with S1 nuclease; (f) denaturing undigested hybrids generated in step (e) and hybridizing them at an appropriate $C_ot$ with single-stranded cDNA inserts amplified in step (b); (g) separating the unhybridized single-stranded cDNA inserts from hybridized cDNA inserts, thereby generating a cDNA population enriched in sequences representing rare mRNAs (FIG. 3); (h) denaturing hybrids generated in step (e) and hybridizing them to an appropriate $C_ot$ with single-stranded circles generated in step (c); and (i) separating the unhybridized single-stranded circles from partial duplexes by hydroxyapatite chromatography, and using these single-stranded circles to generate a cDNA library enriched in clones representing rare mRNAs (FIG. 4).

Methods of constructing cDNA libraries are well known, and may be achieved by using commercially available kits (e.g., Promega Universal Riboclone® cDNA synthesis system). The applicant's method uses cDNA libraries constructed with lambda gt11 and lambda ZapII™ vectors (Stratagene, La Jolla, Calif.). Methods of amplification of single-stranded and double-stranded cDNAs from cDNA libraries by PCR are also well known. Single-stranded and double-stranded cDNA inserts were amplified from a lambda gt11 cDNA library. Double-stranded cDNA inserts were amplified from the lambda ZapII™ cDNA library as well. Also, the double-stranded cDNA library in lambda ZapII™ was converted into single-stranded circles in vivo by well-known methods.

Conditions under which denatured cDNAs reassociate with complementary ones to produce hybrids are well known. We hybridized denatured abundant cDNA inserts with (1) target single-stranded cDNA inserts, and (2) target single-stranded circles in 0.3 M sodium phosphate (pH 7.0) at 65° C. to $C_o$ts 20–380.

S1 nuclease degradation of single-stranded DNAs or single-stranded regions of partial duplexes is well known. We diluted reassociation mixtures to a volume at which sodium phosphate does not inhibit Si activity. After S1 treatment, undisgested double-stranded cDNA hybrids are used as the "abundant cDNA pool" or "abundant cDNAs". As used herein, "abundant cDNA pool" or "abundant cDNAs" mean sets of cDNAs enriched in abundant cDNAs in comparison with sets of unnormalized cDNAs. By contrast, "rare cDNAs" means a set of cDNAs that is enriched in rare cDNA sequences. These cDNAs, remaining as single-stranded molecules after partial reassociation with an abundant cDNA pool, and include some abundant sequences.

Methods of subtraction of cDNAs are well known in the art. In method 1, single-stranded cDNA inserts generated from the lambda gt11 cDNA library are hybridized with an excess of abundant cDNA inserts generated from the lambda ZapII™ cDNA library. In method 2, single-stranded circles generated from the lambda ZapII™ cDNA library are hybridized with an excess of abundant cDNA inserts generated from the lambda gt11 cDNA library.

Methods of separating single-stranded DNA from double-stranded DNA are well known in the art. In this work, single-stranded DNAs are eluted from the hydroxyapatite (HAP) column by 0.15 M sodium phosphate (pH 7.0) at 60° C.

This invention provides two products. The product of method 1 is two sets of cDNAs from the dauer stage of *C. elegans* averaging 300 base pairs in length, which have been shown by hybridization analysis to be enriched in sequences representing rare messenger RNAs. The product of method 2 is a subtractive cDNA library with inserts averaging 800 base pairs, which is enriched for rare sequences as judged by the following comparisons. First, ten of twenty sequenced clones correspond to genes predicted from the genomic sequence, but for which no EST has been detected in the existing set of 118,000. Although ESTs have been identified for only 50% of the predicted 19,000 genes in *C. elegans*, the previous *C. elegans* normalized libraries are now yielding only one new gene in 20 sequenced cDNA clones. Second, comparison of the sequenced clones with the Serial Analysis of Gene Expression (SAGE) in the dauer stage reveals that none of the clones correspond to abundantly expressed genes. Third, hybridization analysis with the 20 sequenced clones, and several control abundant clones, showed enrichment in concentrations of rare clones up to 197-fold, whereas abundant clones as a rule were not detected.

The cDNA library generated in method 2 was derived from mRNA isolated from the dauer stage of *C. elegans*. A direct comparison with unnormalized dauer mRNA uses the data set generated by SAGE in the dauer stage. The SAGE analysis provides a catalog of the genes expressed and the relative abundance of sequence tags for each gene. Fourteen of the clones sequenced in the subtractive library that corresponded to predicted genes had no SAGE tags, indicating they are expressed at a level at least 4000-fold lower than the most abundantly expressed genes in the dauer stage.

The practice of the present invention will employ, unless otherwise indicated, conventional techniques of molecular biology, microbiology and recombinant DNA technology which are within the skill of the art. Such techniques are explained fully in the literature. See, e.g., Sambrook, Fritsch & Maniatis, Molecular Cloning: A Laboratory Manual, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I–IV (D. M. Weir and C. C. Blackwell eds., 1986, Blackwell Scientific Publications).

As used in this specification and the appended claims, the singular forms "a," "an" and "the" include plural references unless the content clearly dictates otherwise.

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extra-chromosomal plasmids. This stability is demonstrated by the ability of the eucaryotic cell to establish cell lines or clones comprised of a population of daughter cells containing the exogenous DNA.

The transformation procedure used depends upon the host to be transformed. Mammalian cells can conveniently be transformed using, for example, DEAE-dextran based procedures, calcium phosphate precipitation (Graham, F. L. and Van der Eb, A. J. (1973) Virology 52:456–467), proto-plast fusion, liposome-mediated transfer, polybrene-mediated transfection and direct microinjection of the DNA into nuclei. Bacterial cells will generally be transformed using calcium chloride, either alone or in combination with other divalent cations and DMSO (Sambrook, Fritsch & Maniatis, Molecular Cloning: A Laboratory Manual, Second Edition (1989)). DNA can also be introduced into bacterial cells by electroporation. Methods of introducing exogenous DNA into yeast hosts typically include either the transformation of spheroplasts or transformation of intact yeast cells treated with alkali cations.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 $\mu$g of plasmid or DNA sequences is cleaved by one unit of enzyme in about 20 $\mu$l of buffer solution. Typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980). Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in 50 mM Tris (pH 7.6) 50 mM NaCl, 6 mM $MgCl_{2,\ 6}$ mM DTT and 5–10 $\mu$M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 10–50 $\mu$l volumes under the following standard conditions and temperatures using T4 DNA ligase. Ligation protocols are standard (D. Goeddel (ed.) Gene Expression Technology: Methods in Enzymology (1991)). In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, re-ligation can be prevented in vectors which have been double digested by additional restriction enzyme digestion of the unwanted fragments.

Advantages. Technical Impact and Improvements Which Invention Provides

The main advantage of the invention is that it can increase the concentration of rare cDNAs several times more than has been achieved for other methods. For example, in the method of Ko et al. (1990) the increase for rare cDNAs was up to 2.6-fold, in the method of Patanjali et al. (1991) the increase was 3-fold, and in the method of Sasaki et al. (1994) the increase was up to 6-fold. In the method most similar to the applicant's (Bonaldo et al., 1996; Soares et al., U.S. Pat. No. 5,846,721), the increase was 12–30 fold. The applicant's method 1 resulted in an increase of up to 94 fold for rare cDNAs. Method 2 resulted in an increase of up to 197-fold for rare cDNAs. Sequencing 20 random clones from a cDNA library subjected to removal of abundant clones by method 2 revealed that half of them represented genes not previously detected by the *C. elegans* EST sequencing project (Kohara et al. 1999; see also http://alpha.crbm.cnrs-mop.fr). This project has sequenced 65,000 cDNA clones from libraries normalized by other methods, and these correspond to about half of the 19,000 predicted genes in the *C. elegans* genome.

The method presented herein as the invention is much simpler than that of Bonaldo et al. (1996), which involves two steps of in vitro transcription after construction of the cDNA library (the present invention does not contain this step), two or three transformations of *E. coli* strains (the invention presented herein involves one), and three hydroxyapatite chromatography steps (the method presented herein requires only one). Also, the method presented herein avoids the use of blocking oligonucleotides used in two steps of the Bonaldo et al. (1996) method.

A key enabling aspect of this invention is the method to create a high-quality, abundant cDNA pool. This involves the novel use of S1 nuclease digestion (rather than HAP-chromatography) for elimination of single-stranded DNA from a mixture of single-stranded and double-stranded molecules. This is important because contaminating rare sequences present in the abundant pool would result in undesirable subtraction of these sequences during the subsequent subtractive hybridization step. Attempts by Soares et al. (U.S. Pat. No. 5,846,721, and described by Bonaldo et al., 1996) to generate a high-quality abundant cDNA pool involved many steps that we eliminate, including in vitro transcription, and HAP-chromatography.

It is important to note that a method (like the one presented herein) which is shorter and simpler is a great improvement over pre-existing method because the greater number of manipulations which are required, the greater loss of final yield at each step. The starting material (mRNA) may have only very, very few mRNA molecules which represent a particular expressed gene. Therefore, in order to capture these mRNAs in the final "rare cDNA pool" which is the product of the method presented herein, it is imperative to perform the method is as simple and as short a way as possible. Rare cDNAs could easily be lost due to routine experimental loss if the starting material (mRNA) is subjected to many complicated steps and manipulations.

New cDNA resources are urgently needed for genome research. Complete sets of cDNA sequences for both humans and model organisms will be extremely useful both for gene discovery and for functional studies. A major limitation to current genome research is that identifying genes expressed at very low levels is a very difficult and expensive task. This invention is a significant technological development to make detection of such genes a practical reality, and its potential impact on genome research is enormous.

The present invention will be important for use in genome sequencing and gene discovery projects, gene expression studies and DNA microarray analysis. With regard to genome projects, the present invention will assist in the acceleration of the discovery of new genes, allowing cloning and characterization of human disease genes and plant or animal genes of importance to food production. With regard to gene expression studies, the present invention will allow facilitation of rare gene discovery. Such studies are of importance to understanding developmental and disease processes in plants and animals. cDNA libraries enriched for rare sequences will be of great importance to the analysis of gene expression patterns with DNA microarrays. First, EST-based microarrays currently lack representation of many genes expressed at low levels. Second, use of subtracted libraries for hybridization with microarrayed cDNAs should greatly improve the sensitivity of this method.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Experimental Methods

Preparation of RNA

Preparation of dauer larvae. Five L4 worms of the wild-type N2 strain of *Caenorhabditis elegans* were incubated for 10 days at 20° C. in 4 ml of 4% *E. coli* χ1666 in S medium [1 ml of 1 M potassium citrate, pH 6.0, 1 ml of 100×Trace Metals (2.5 mM $FeSO_4.7H_2O$, 5 mM $Na_2EDTA$, 1 mM $MnCl_2.4H_2O$, 0.1 mM $CuSO_4.5H_2O$), 0.3 ml of 1 M $CaCl_2$, 0.3 ml of 1 M $MgSO_4$ were added to every 100 ml of S Basal medium (5.84 gm of NaCl, 50 ml of 1 M $KH_2PO_4$, pH 6.0, 1 ml of 5 mg/ml cholesterol per liter of aqueous medium)]. The resulting population of dauer larvae was added to 250 ml of the same medium and incubated at 25° C. for the next 10 days.

The culture consisting primarily of dauer larvae was put on ice, and the worms were allowed to settle for 30 min. The settled worms were layered on the top of 30 ml of cold 30% sucrose in M9 buffer (22 mM $KH_2PO_4$, 42 mM $Na_2HPO_4$, 1 mM $MgSq_4$ and 85 mM NaCl) in a sterile Fisher 50 ml Falcon polypropylene centrifuge tube and centrifuged in a Beckman GPR centrifuge with a GH 3.7 horizontal rotor at 3500 rpm for 2 min at 4° C. The sucrose floatation step was repeated 2–7 more times. Finally, the layer of purified dauer larvae was placed in 30 ml of cold M9 buffer and centrifuged as above. The packed dauer larvae were kept at 4° C. for several days for the purpose of inoculating cultures for RNA preparation.

For preparation of more synchronized dauer larvae, approximately 125 μl of the packed dauer larvae were seeded into each of two 1 L baffled flasks with 250 ml of 4% *E. coli* χ1666 in S medium and incubated at 25° C. for 6 days. These cultures were then put on ice, and the worms were allowed to settle for 30 min. The settled worms were loaded onto 30 ml of cold (4° C.) 30% sucrose and centrifuged as above. This step was repeated 2–7 more times. Finally, the layer of purified dauer larvae was placed in 30 ml of cold M9 buffer, and centrifuged as above (the final prep did not contain more that one animal of any other stage of *C. elegans* per 500 dauer larvae). The settled dauer larvae (5 ml) were quick-frozen by dripping into liquid nitrogen and stored at −80° C.

Preparation of total RNA from dauer larvae. 1.5 ml of packed frozen worms were crushed in liquid nitrogen using a mortar and pestle for 5–10 min. 20 ml of solution D (4 M guanidium thiocyanate, 25 mM sodium citrate, pH 7.0, 0.5% sarcosyl, 0.1 M 2-mercaptoethanol), 2 ml of 2 M sodium acetate, pH 4.0, 20 ml of phenol saturated in water with 8-hydroxyquinolone added to 1 mg/ml and 2-mercaptoethanol added to 60 mM, and 4 ml of chloroform/isoamyl alcohol (24:1) were added to the crushed worms. The mixture was vigorously shaken in a 50 ml polypropylene centrifuge tube for 2 min and cooled on ice for 15 min. After centrifugation in the GH 3.7 rotor at 3500 rpm for 10 min at 4° C., the upper phase was collected and added to an equal volume of a mixture containing 24:24:1 phenol (with 0.2 M sodium acetate, pH 4.0, 1 mg/ml 8-hydroxyquinolone and 60 mM 2-mercaptoethanol): chloroform/isoamyl alcohol in a 50 ml tube. This mixture was vigorously shaken for 2 min and centrifuged as above. The aquatic phase was added to an equal volume of cold isopropyl alcohol and kept at −20° C. for 1 hour to precipitate the nucleic acids. (All references to "cold" alcohol refer to alcohol prechilled to −20° C.) After centrifugation in a JA-20 rotor in a Beckman J2-21M/E centrifuge at 20,000 rpm for 20 min at 4° C., the supernatant was removed. The pellet was dissolved in 5 ml of solution D, then precipitated by an equal volume of cold isopropyl alcohol at −20° C. for 30 min, and centrifuged at 10,000 rpm for 10 min at 4° C. The pellet was dissolved in 5 ml of DEPC-treated distilled water, and RNA was precipitated in 0.5 ml of 3 M sodium acetate, pH 5.0 and 13 ml of cold ethanol for 1 hour. The sample was centrifuged at 10,000 rpm for 10 min at 4° C. The pellet was washed with 70% cold ethanol, dried and dissolved in 5 ml of DEPC-treated distilled water. 15 ml of cold ethanol were added to the solution of total RNA, and the mixture was stored at −80° C. The yield of total RNA from 5 ml of settled dauer larvae was approximately 12 mg.

Preparation of poly(A)-enriched RNA. Total RNA was recovered from the 20 ml volume (above) by adding 0.5 ml of 3 M sodium acetate, pH 5.0, and centrifuged in a JA-20 rotor at 10,000 rpm for 10 min at 4° C. The pellet was washed by cold 70% ethanol, dried and dissolved in 4 ml of loading buffer (0.3 M NaCl, 10 mM Tris.HCl, pH 7.5, 1 mM EDTA, 1% SDS). The total RNA was heated at 65° C. for 5 min and replaced on ice. The cooled total RNA was loaded onto a column containing 1 ml of oligo(dT)-cellulose type 7 (Pharmacia). The column was washed with 10 volumes of loading buffer, and poly (A)-containing RNA was then eluted with 10 ml of 10 mM Tris.HCl, pH 7.5, 1 mM EDTA, 0.2% SDS in 0.5 ml fractions. Approximately 400 $\mu$g of poly(A)-enriched RNA were collected. NaCl was added to the eluate to 0.3 M, and chromatography was repeated once using the same column. Poly(A)-containing RNA was precipitated twice in ethanol with sodium acetate, pH 5.0, and stored in distilled water at −80° C. The final yield was 250 $\mu$g of poly(A)-enriched RNA.

cDNA Synthesis.

Synthesis of the first cDNA strand. cDNA was synthesized using a Promega Universal Riboclone cDNA synthesis kit. 10 $\mu$g of poly(A)-enriched RNA were mixed with 5 $\mu$g of oligo(dT)$_{15}$ primer in 75 $\mu$l of water. The mixture was heated at 70° C. for 5 min and placed on ice. 25 $\mu$l of 5× first-strand buffer [250 mM Tris.Hcl, pH 8.3 (at 42° C.), 250 mM KCl, 50 mM MgCl$_2$, 2.5 mM spermidine, 50 mM DTT, 5 mM each of DATP, dCTP, dGTP, dTTP], 5 $\mu$l (200 units) of RNasin ribonuclease inhibitor, 12.5 $\mu$l of 40 mM sodium pyrophosphate, 6 $\mu$l (150 units) of AMV reverse transcriptase, and 1.5 $\mu$l of water were added to the mixture of poly(A)-containing RNA with oligo (dT)$_{15}$ primer. First-strand synthesis was conducted at 42° C. for 1.5 hours, and the reaction was placed on ice.

Synthesis of the second cDNA strand. The following components were added to the first-strand synthesis reaction in order: 250 $\mu$l of 2.5× second-strand buffer (100 mM Tris.HCl, pH 7.2, 225 mM KCl, 7.5 mM MgCl$_2$, 7.5 mM DTT, 0.125 mg/ml bovine serum albumin), 14.5 $\mu$l (145 units) of DNA Polymerase I, 2.5 $\mu$l (5 units) of RNase H and 232 $\mu$l of water. Second-strand synthesis was conducted at 14° C. for 4 hours. The reaction was then heated at 70° C. for 10 min and placed on ice. 2 $\mu$l (20 units) of T4 DNA Polymerase were added, and the reaction was incubated at 37° C. for 10 min. The reaction was stopped by adding 69 $\mu$l of 200 mM EDTA, and it was placed on ice.

The cDNA was extracted in a 1.5 ml microcentrifuge tube with an equal volume of TE (10 mM Tris.HCl, pH 8.0, 1 mM EDTA)-saturated phenol/chloroform/isoamyl alcohol (24:24:1). The tube was centrifuged at 16,000 g in a microcentrifuge for 2 min at room temperature. The aqueous phase was transferred to a fresh tube, and the cDNA was precipitated by adding 3 M sodium acetate, pH 5.0 to 0.3 M, and 2.5 volumes of cold ethanol and kept for 1 hour at −20° C.

The cDNA was recovered by centrifugation in a microcentrifuge at 16,000 g for 6 min at room temperature. The pellet was washed with cold 70% ethanol, dried and dissolved in 50 $\mu$l of TEN (10 mM Tris.HCl, pH 8.0, 1 mM EDTA, 100 mM NaCl). cDNAs of less than 400 bp were removed by spin chromatography with a Sephacryl S-400 column (Promega). The solution containing the cDNA was loaded onto a spin column and centrifuged in the GPR centrifuge at 2000 rpm for 5 min. The eluted cDNA was precipitated by adding 3 M sodium acetate, pH 5.0 to 0.3 M, and 2.5 volumes of cold ethanol.

Library Construction and Phage DNA Preparation.

Ligation of the cDNA with EcoRI adaptors. The cDNA was recovered by centrifugation in a microcentrifuge at 16,000 g for 6 min at room temperature. The pellet was washed with cold 70% ethanol, dried and dissolved in 11.5 $\mu$l water. 10 $\mu$l (1000 ng) of the cDNA solution were mixed with 3 $\mu$l of 10×T4 DNA ligase buffer (300 mM Tris.HCl, pH 7.8, 100 mM MgCl$_2$, 100 mM DTT, 5 mM ATP), 3 $\mu$l of acetylated bovine serum albumin, 1 mg/ml, 6 $\mu$l (60 pmoles) of EcoRI adaptors, 1 $\mu$l (3 units) of T4 DNA ligase and 7 $\mu$l of water. EcoRI adaptors were ligated with the cDNA at 15° C. overnight. The T4 DNA ligase was inactivated by heating the reaction mixture to 70° C. for 10 min, and the reaction mixture was cooled on ice.

Phosphorylation of the cDNA. Phosphorylation was conducted in a 0.5 ml PCR tube by mixing the cDNA ligated with EcoRI adaptors with 4 $\mu$l of 10×T4 Polynucleotide Kinase buffer (700 mM Tris.HCl, pH 7.6, 100 MM MgCl$_2$, 50 mM DTT), 2 $\mu$l of 0.1 mM ATP, 1 $\mu$l (10 units) of Polynucleotide Kinase and 3 $\mu$l of water. The reaction mixture was incubated at 37° C. for 30 min, and the phosphorylated cDNA was extracted with an equal volume of TE-saturated phenol:chloroform:isoamyl alcohol (24:24:1). The tube was centrifuged at 16,000 g for 2 min at room temperature. The aqueous phase was transferred to a fresh tube, and the cDNA was precipitated for 1 hour at −20° C. after addition of 3 M sodium acetate, pH 5.0 to 0.3 M and 2.5 volumes of cold ethanol.

To remove the excess EcoRI adaptors, the phosphorylated cDNA was recovered by centrifugation at 16,000 g for 6 min at room temperature. The pellet was washed with cold 70% ethanol, dried and dissolved in 50 $\mu$l of TEN. EcoRI adaptors were removed by spin chromatography with a Sephacryl S-400 column (Promega). The solution containing the phosphorylated cDNA and excess of EcoRI adaptors was loaded onto a spin column and centrifuged in the GPR centrifuge at 2000 rpm for 5 min. The eluted cDNA was precipitated by adding 3 M sodium acetate, pH 5.0 to 0.3 M, and 2.5 volumes of cold ethanol, and recovered by centrifugation for 6 min at room temperature. The pellet was washed with cold 70% ethanol, dried and dissolved in 11 $\mu$l of water.

Cloning cDNA into lambda gt11 and lambda ZapII™ vectors.

Construction of cDNA libraries from dauer larvae was conducted using Stratagene lambda gt11/EcoRI/CIAP-treated and lambda ZapII™ predigested EcoRI/CIAP-treated vector kits and Gigapack III Gold™ packaging extract. 50 ng of cDNA were ligated with 2 μg of lambda gt11 or lambda ZapII™ using 4 units of T4 DNA ligase in 10 μl of T4 ligase buffer (30 mM Tris.HCl, pH 7.8, 10 MM MgCl$_2$, 10 mM DTT, 0.5 mM ATP) at 14° C. overnight.

A single colony of *E. coli* Y1088 or *E. coli* XL1-Blue™ MRF' was used to inoculate 25 ml of LB broth (10 g of NaCl, 10 g of tryptone, 5 g of yeast extract per 1 liter, pH 7.0), supplemented with 10 mM MgSO$_4$ and 0.2% (w/v) maltose. The bacteria were allowed to grow with shaking for 4–6 hours at 37° C. The bacteria were then centrifuged in a 50 ml tube in the GH 3.7 rotor at 2000 rpm for 10 min, and the pellet was gently resuspended in 12.5 ml 10 mM MgSO$_4$ and diluted with 10 mM MgSO$_4$ to an OD$_{600}$ of 0.5.

Each ligase mixture was added to its own 75 μl packaging extract and incubated at room temperature (22° C.) for 100 min. The assembled phages were diluted with SM buffer (5.8 g of NaCl, 2 g of MgSO$_4$.7H$_2$O, 50 ml of 1 M Tris.HCl, pH 7.5, 5 ml of 2% (w/v) gelatin per 1 liter) to 1.5 ml and 60 μl of chloroform were added to each preparation. After centrifugation at 3000 g for 1 min, the supernatants containing the phages were added to 9 ml of *E. coli* Y1088 (for lambda gt11) or *E. coli* XL1-Blue™ MRF' (for lambda ZapII™) and incubated at 37° C. for 15 min. The infected cells were then mixed with 97.5 ml of melted top agar cooled to 48° C. [7 g of agarose in 1 liter of NZCYM (10 g of NZ amine A, 5 g of NaCl, 5 g of yeast extract, 1 g of casamino acids, 2 g of MgSO$_4$.7H$_2$O, pH 7.5 per 1 liter)], supplemented with 0.2% maltose. Each mixture was spread evenly onto 15 150 mm (Fisher) LB agar plates (15 g of agar in 1 liter of LB broth: 10 g of NaCl, 10 g of tryptone, 5 g of yeast extract per 1 liter, pH 7.0), supplemented with 0.2% maltose. The plates were incubated at 37° C. for 8 hours. The lambda gt11 cDNA library from *C. elegans* dauer larvae contained more than 500,000 independent recombinant clones with an average insert size of about 910 bp; the cDNA library in lambda ZapII™ contained nearly 1 million independent recombinant clones, with an average insert size of about 950 bp.

The phage were recovered from each plate by incubation overnight at 4° C. with 10 ml of SM buffer. The plates were rinsed with 2 ml of SM buffer and pooled into 50 ml Falcon tubes. Chloroform was added to a 5% (v/v) final concentration. The contents were mixed and incubated at room temperature for 15 min. The cell debris was removed by centrifugation at 3500 rpm for 10 min in the GH 3.7 rotor. Dimethylsulfoxide (DMSO) was added to a final concentration of 7% (v/v). The cDNA libraries were stored at −80° C.

Preparation of phage DNA. A single colony of *E. coli* Y1088 or XL1-Blue MRF' was inoculated into 50 ml of NZCYM medium. The cells were incubated with shaking at 37° C. overnight, and two aliquots from each culture containing $10^{10}$ cells (1 OD$_{600}$=8×$10^8$ cells/ml) were centrifuged at 2000 rpm for 10 min in the HR 3.7 rotor. Each bacterial pellet was resuspended in 3 ml of SM. 5×$10^7$ pfu from lambda gt11 or lambda ZapII phage libraries were added to each aliquot, mixed rapidly, and incubated at 37° C. for 20 min with intermittent shaking. Each infected aliquot was added to 500 ml of NZCYM, prewarmed to 37° C. in a 2-liter flask and incubated at 37° C. overnight.

When lysis was apparent, 10 ml of chloroform were added to each flask, incubation was continued for 10 min, and the lysed cultures were cooled to room temperature. Pancreatic DNAase I (Sigma) and RNAase (Sigma) were added, each to a final concentration of 1 μg/ml, and after incubation at room temperature for 30 min, NaCl was added to a final concentration of 1 M (the NaCl was dissolved by swirling).

The flasks were kept on ice for 1 hour, and the suspensions were centrifuged in the Beckman JA-10 rotor at 10,000 rpm for 10 min at 4° C. The supernatants were pooled in clean flasks, and 50 g of polyethylene glycol (PEG 8000) were added by slow stirring at room temperature to a final concentration of 10% (w/v). The flasks were kept in ice water for 1 hour to allow the bacteriophage to form a precipitate. The precipitated bacteriophage were recovered by centrifugation as above. The supernatants were removed, and the pellets from each initial 500 ml culture were gently resuspended in 5 ml of TM buffer (50 mM Tris.HCl, pH 7.8, 10 mM MgSO$_4$). An equal volume of chloroform was added, and each suspension was vortexed for 30 seconds. The organic and aquatic phases were separated by centrifugation in the JA-20 rotor at 6,500 rpm for 15 min at 4° C. The aquatic phases were layered on glycerol step gradients in Beckman SW41 polycarbonate tubes (each tube contained 3 ml of 40% glycerol in TM on the bottom and 4 ml of 5% glycerol in TM on the top). The tubes were centrifuged at 35,000 rpm for 60 min at 4° C. in a Beckman SW41 rotor. The supernatants were removed, and the bacteriophage pellets were dissolved in 1 ml of TM per liter of original culture.

Pancreatic DNAase I (Sigma) and RNase (Sigma) were added to final concentrations of 5 μg/ml and 1 μg/ml, respectively, and digestion was conducted for 30 min at 37° C. Then, EDTA (pH 8.0) was added to a final concentration of 20 mM, Proteinase K (Boehringer Mannheim) was added to a final concentration of 50 μg/ml, and SDS (sodium dodecylsulfate) was added to a final concentration of 0.5%. The solutions were mixed by inverting the tubes, incubated at 56° C. for 1 hour, then cooled to room temperature. An equal volume of phenol equilibrated with 50 mM Tris.HCl (pH 8.0) was added, and the phases were mixed by inverting the tubes repeatedly for 1 min until complete emulsions were formed. The phases were separated by centrifugation at 3000 g in a microcentrifuge for 5 min. The aqueous phases were extracted once with an equal volume of a 50:50 mixture of equilibrated phenol and chloroform. After centrifugation at 3000 g for 5 min the aqueous phases were again recovered and extracted once with an equal volume of chloroform and centrifuged as above.

The aqueous phases were transferred to dialysis bags (Pierce) and dialyzed overnight at 4° C. against three changes of a 1000-fold volume of TE buffer. After dialysis, 3 M sodium acetate (pH 5.0) was added to a final concentration of 0.3 M and 2.5 volumes of cold ethanol were added. The solutions were kept at room temperature for 30 min, and phage DNA was recovered by centrifugation at 12,000 g for 2 min at room temperature in a microcentrifuge. The pellets were washed with cold 70% ethanol, dried and dissolved in distilled water. The aqueous solutions of phage DNAs were stored at −20° C.

Preparation of Abundant cDNA Pools

Primers. The following primer pairs were used to amplify cDNA inserts: F11, 5'-CTCCTGGAGCCCGTCAGTAT-3' (SEQ ID NO:1) and R11, 5'-GTAATGGTAGCGACCGGCGC-3' (SEQ ID NO:2); and the nested primer pair FC11, 5'-GGAGCCCGTCAGTATCGGCG-3' (SEQ ID NO:3) and RC11, 5'-GTAGCGACCGGCGCTCAGCT-3' (SEQ ID NO:4) were used to amplify lambda gt11 inserts; and KSL, 5'-TCGAGGTCGACGGTATCGAT-3' (SEQ ID NO:5) and SKL, 5'-CCGCTCTAGAACTAGTGGATC-3' (SEQ ID NO:6) were used to amplify lambda ZapII™ inserts.

PCR of cDNA inserts in lambda gt11 or lambda ZapII™ cDNA libraries. PCR of lambda ZapII™ cDNA inserts was conducted in aliquots of 50 μl Taq Polymerase buffer containing 140–250 ng of phage DNA, 200 ng each of KSL and SKL primers, and 2 units of Taq Polymerase (Sigma), either with or without 10% DMSO. Initial denaturation was at 96° C. for 3 min followed by 30 cycles (95° C. for 1 min; 64° C. for 1 min; 72° C. for 2 min) and a final extension at 72° C. for 5 min. The amplified cDNA inserts were extracted with 50 μl of phenol/chloroform/isoamyl alcohol (24:24:1) and precipitated with ethanol. The pellet of the amplified cDNA inserts was dissolved in water and stored at −20° C.

PCR of lambda gt11 cDNA inserts was carried out in two steps. The first round was performed in aliquots of 50 μl containing Taq Polymerase buffer, 2 μg of phage DNA, 200 ng each of F11 and R11 primers, and 2 units of Taq Polymerase (Sigma) with 3% DMSO. PCR was performed as above, but with 10 cycles instead of 30. After extraction and precipitation as above, the pellet of the amplified cDNA inserts was dissolved in TEN buffer. Amplified cDNA inserts less than 400 bp were removed by spin chromatography with a Sephacryl S-400 column (Promega). A second round of PCR was conducted in aliquots of 50 μl containing Taq Polymerase buffer, 2 μl of cDNA inserts amplified in the first step, 200 ng each of F11 and R11 primers, and 2 units of Taq Polymerase with 4% DMSO. PCR was performed as above, but with 20 cycles. The amplified cDNA was extracted and precipitated as above, and the pellet was dissolved in water and stored at −20° C.

Removal of common sequences from the ends of amplified cDNA is inserts. 133–200 μg of the amplified cDNA inserts from lambda gt11 or lambda ZapII™ cDNA libraries were digested with 300–360 units of EcoRI in 300–360 μl of EcoRI buffer (90 mM Tris.HCl, pH 7.5, 50 mM NaCl, 10 MM $MgCl_2$) at 37° C. for 2–4 hours. After phenol/chloroform/isoamyl alcohol treatment, the cDNAs were precipitated with ethanol. The cDNA pellet was dissolved in water and stored at −20° C.

Partial reassociation. Two protocols were used for partial reassociation. First, 130–200 μg of EcoRI-digested cDNAs in 20–24 μl of water were denatured at 96–99° C. for 1.5–2 min. 2 M sodium phosphate (pH 7.0) was added to a final concentration of 0.3 M, and denaturation was continued for another 1.5–2 min. Partial reassociation was conducted at 65° C. for 2–3 hours. Second, 150 μg EcoRI-digested cDNAs in 11.76 μl of 0.3 M sodium phosphate (pH 7.0) were denatured at 99° C. for 3 min, and partially reassociated was conducted at 65° C. for 3 hours.

S1 nuclease treatment. The mixtures of reassociated and unreassociated cDNAs were diluted in water to a volume of 200–420 μl and added to an equal volume of 2×S1 buffer (66 mM sodium acetate, pH 4.5, 100 mM NaCl, 0.06 mM $ZnSO_4$). 150–400 units of S1 nuclease (Boehringer Mannheim) were added, and the digestion was conducted at 37° C. for 1.5–2 hours. Double-stranded hybrids were treated by phenol/chloroform/isoamyl alcohol and precipitated with ethanol. The pellets of abundant cDNAs were dissolved in water and stored at −20° C.

Preparation of Target cDNAs

Preparation of target single-stranded cDNAs from lambda gt11 library. Target cDNAs were amplified in 50 μl containing Taq Polumerase buffer, 3 μg of phage DNA, 200 ng of F11 primer, and 2 units of Taq Polymerase, with or without 10% DMSO. For amplification, an initial denaturation at 96° C. for 3 min was followed by five cycles (95° C. for 1 min; 64° C. for 1 min; 72° C. for 3 min) and a final extension at 72° C. for 5 min. The amplified cDNA inserts were treated by phenol/chloroform/isoamyl alcohol and precipitated by ethanol. The pellets of single-stranded cDNAs were dissolved in water and stored at −20° C.

Preparation of single-stranded circles from lambda ZapII™ cDNA library. The Stratagene protocol and kit for in vivo excision of the pBluescript SK(−) phagemid from the lambda ZapII™ vector were used. Cultures of XL1-Blue™ MRF' and SOLR cells were grown overnight at 30° C. in LB broth supplemented with 0.2% maltose and 10 mM $MgSO_4$. The cells were gently spun at 1000 g and resuspended in 10 mM $MgSO_4$ to an $OD_{600}$ of 1.0 ($8\times10^8$ cells/ml). $5\times10^7$ pfu (20 μl) of the lambda Zap™ library were combined with $10^8$ XL1-Blue MRF' cells and $10^8$ ExAssist™ phage in a 50 ml conical tube, and incubated at 37° C. for 15 min to allow adsorption. 20 ml of LB broth were added, and incubation was continued for 3 hours at 37° C. with shaking. After heating the conical tube at 65° C. for 20 min, the debris was spun down at 1000 g for 10 min and the supernatant, containing the excised pBluescript™ phagemid packaged as filamentous phage particles, was decanted into a sterile conical tube. 200 μl of SOLR cells were infected with 100 μl of this supernatant, the mixture was incubated at 37° C. for 15 min, then added to 25 ml of LB broth with 50 μg/ml ampicillin, and incubated at 37° C. overnight. Double-stranded plasmid DNA was prepared using a PE Applied Biosystems™ miniprep kit as recommended by the manufacturer.

To convert double-stranded plasmid DNA into single-stranded pBluescript™ SK(−), 0.2 μg of double-stranded plasmid DNA were electroporated into competent XL1-Blue™ MRF' cells. This amount of plasmid DNA was used to ensure that few clones would be lost and that a representative library would be produced. The cells were incubated overnight on 20 150 mm diameter LB agar plates containing 50 μg/ml ampicillin. About 2,000,000 independent recombinant clones were washed from the plates with 2× YT broth (16 gm tryptone, 10 gm yeast extract, and 5 gm NaCl per 1 liter). 50 μl of this cell suspension of 20 $OD_{600}$/ml were mixed with 10 μl ($10^9$) of VCSM13 helper phage and added to 10 ml of 2× YT broth with 50 μg/ml ampicillin. The culture was allowed to grow at 37° C. for 1 hour, then kanamycin was added to a final concentration of 70 μg/ml, and incubation was continued for 20 hours. The culture was microcentrifuged at 21,000 g for 5 min, and 6 ml of the supernatant were mixed with 900 μl of 20% polyethylene glycol (PEG 8000) in 2.5 M NaCl. The phage particles were allowed to precipitate on ice for 15 min, then were microcentrifuged for 5 min. The pellet was dissolved in 2.4 ml 0.3 M sodium acetate (pH 6.0), 1 mM EDTA by vortexing. The single-stranded circles were extracted with 1 volume of phenol/chloroform/isoamyl alcohol and microcentrifuged at 21,000 g for 2 min to separate the phases. The aqueous phase was transferred to fresh microcentrifuge tubes, and 2.5 volumes of ethanol were added. The suspension was microcentrifuged at 21,000 g for 5 min, the supernatant was removed, and the pellet was rinsed by 70% cold ethanol and dried. The DNA of single-stranded pBluescript™ SK(−) was dissolved in TE buffer and stored at −20° C.

Preparation of Rare cDNAs and Rare Single-stranded Circles.

Subtraction. Two types of subtractive protocols were used. They involved single-stranded cDNA amplified from the lambda gt11 library, or single-stranded recombinant circles prepared from the lambda ZapII™ library as a target DNA (methods 1 and 2, respectively). For method 1, two subtractive protocols were used. The first protocol used a single round of subtraction, and the second used four rounds, as follows: (a) 40 ng of single-stranded cDNA from the lambda gt11 cDNA library were mixed with 8 μg of the abundant cDNA pool prepared from the lambda ZapII™ cDNA library in a volume of 2 µl of 0.3 M sodium phosphate, pH 7.0. The cDNA mixture was denatured at 99° C. for 3 min, partially reassociated at 65° C. for 30 min, then diluted with water to a sodium phosphate concentration of 10 mM. This procedure was used to produce the "rare" cDNA tested in FIG. 5. (b) First, 50 ng of single-stranded cDNA from the lambda gt11 library were mixed with 5 µg of abundant lambda ZapII™ cDNA in 7 µl of 0.3 M sodium phosphate, pH 7.0. Second, the mixture of cDNAs was denatured as above, and partially reassociated at 65° C. for 5 min. Third, 5 µg of abundant lambda ZapII™ cDNA (denatured at 96° C. for 1 min in 5 µl of water) were added. Fourth, 2 M sodium phosphate (pH 7.0) was added to a final concentration of 0.3 M, and the mixture was partially reassociated at 65° C. for 5 min. The third and fourth steps were repeated twice, except that the last reassociation was conducted for 15 min. The mixture was then diluted with water to 10 mM sodium phosphate. This procedure was used to produce the "rare" cDNA tested in FIG. 6.

For subtraction of abundant cDNAs from single-stranded recombinant circles (method 2), 16 µg of abundant cDNA prepared from the lambda gt11 cDNA library were denatured at 94° C. for 1.5 min in a volume of 13.4 µl. Then, 5 µl (100 ng) of the single-stranded circles from the lambda ZapII™ library, and 2.6 µl of 2 M sodium phosphate (pH 7.0) were added. The mixture was denaturated at 94° C. for 1.5 min, partially reassociated at 65° C. for 3 hr, then diluted with water to 10 mM sodium phosphate. This procedure was used to produce the "rare" cDNA tested in FIG. 7.

HAP-chromatography. 1 gm of DNA-Grade Bio-Gel HTP hydroxyapatite (Bio-Rad) was mixed with 10 ml of 10 mM sodium phosphate (pH 7.0), settled for 2 min, and the upper layer containing small particles of hydroxyapatite was discarded. This settling step was repeated nine times. 250 µl of selected hydroxyapatite were loaded into a jacketed Econo-Column™ (Bio-Rad). 60° C. were maintained during HAP-chromatography. The subtraction mixtures of single and double-stranded DNAs were diluted with water to 10 mM sodium phosphate and loaded onto the column for chromatography at 60° C. After washing with 10 ml of 10 mM sodium phosphate (pH 7.0), the bottom of the column was sealed with a stopper and 0.5 ml of 0.15 M sodium phosphate (pH 7.0) were loaded onto the column. The stopper was removed after 5 min, and single-stranded DNAs were collected in a single 0.5 ml fraction.

Desalting and concentrating the single-stranded cDNA fraction. A YM-30 Centricon centrifugal filter (Millipore) was rinsed with distilled water 10 times. 1 ml of yeast tRNA in distilled water (1 µg/ml) was added into the filter and centrifuged in a JA-20 rotor at 5,000 rpm for 20 min at 4° C. The eluate of single-stranded DNA from the HAP column was mixed with 0.5 ml of distilled water, loaded into the filter, and the filter was centrifuged as above. Then, 1 ml of distilled water was added and centrifugation was repeated. This step was repeated once more. Finally, 1 ml of distilled water was added to the filter, and it was centrifuged at 5,000 rpm at for 40 min 4° C., concentrating the material on the filter to about 50 µl. The filter was then inverted, and the desalted and concentrated single-stranded DNAs were collected by centrifugation at 3,000 rpm for 10 min at 4° C.

PCR of rare cDNAs. 5 µl of single-stranded cDNA ("rare" cDNAs) produced by method 1 were amplified by PCR, as described above for amplification of cDNA inserts from the phage libraries, using 200 ng of F11 and R11 (or FC11 and RC11), except that 30–40 cycles (95° C. for 1 min; 64° C. for 1 min; 72° C. for 1–2 min) were used. The amplified cDNA inserts were extracted with phenol/chloroform/ isoamyl alcohol, precipitated by ethanol, dissolved in water, and stored at −20° C.

Hybridization Analysis of Rare cDNAs Produced by Method 1.

Probes. Five *C. elegans* cDNAs were used as probes. Almost full-length daf-1 and daf-4 cDNAs and full-length daf-7 and Hsp 90 cDNAs were amplified by PCR from corresponding recombinant pBluescript™ plasmids using KSL and SKL primers. PCR was conducted as described above for amplification of cDNA inserts from phage libraries, using 25 ng of recombinant plasmid DNA and 200 ng of KSL and SKL primers with 10% DMSO. The amplified cDNA inserts were treated with phenol/chloroform/ isoamyl alcohol, precipitated with ethanol, and dissolved in water. 1.5 µg of the amplified cDNA inserts were digested with 60 units of EcoRI in 200 µl of EcoRI buffer at 37° C. for 10 hours. After extraction with phenol/chloroform/ isoamyl alcohol the cDNAs were precipitated with ethanol, dissolved in water and loaded onto a 1% agarose gel. After gel electrophoresis, cDNA fragments were eluted using a QIAEX II™ Gel Extraction Kit (QIAGEN).

A 3.7 kb fragment of ama-1 cDNA was prepared from a recombinant plasmid containing the full-length cDNA. 5 µg of the recombinant plasmid were digested with 60 units of EcoRI in 100 µl of EcoRI buffer at 37° C. for 2 hours. The digest was loaded on a 1% agarose gel, electrophoresed, and the 3.7 kb fragment was eluted using the QIAEX II kit.

Probe labeling. 20 ng of probe DNA in 15 µl water were denatured at 96° C. for 2 min and replaced on ice. Labeling was conducted at room temperature for at least 2 hours in a mixture of 5 µl of 5×OLB, 1 µl of 10 mg/ml acetylated bovine serum albumin (Promega), 1 µl of Klenow polymerase (Promega), and 3 µl of [α-$^{32}$p] dCTP, 3000 Ci/mmol (NEN). 5× OLB is a mixture of A, B, and C solutions in a ratio of 100:250:150 µl. Solution A consists of 1 ml of 1.25 M Tris.HCl, 0.125 M MgCl$_2$, pH 8.0, plus 5 µl of 100 mM DATP, 5 µl of 100 mM dTTP, and 5 µl of 100 mM dGTP in TE buffer, pH 7.0. Solution B consists of 2 M Hepes, pH 6.6. Solution C consists of hexameric oligonucleotides at 90 OD units/ml (Feinberg and Vogelstein, 1983). Unincorporated [α-$^{32}$p] dCTP was removed by passing the samples over a STE SELECT-D™ G-50 spin column (5 Prime—3 Prime, Inc.) according to the manufacturer's protocol. Probes were denatured at 96° C. for 2 min before use.

Immobilization of cDNAs on nylon membranes. 300–500 ng of amplified unnormalized, rare, or abundant cDNAs were denatured at 60° C. for 30–60 min in 30 µl of 0.3 N NaOH. As a control to quantify the signal from remaining unreassociated cDNA from the abundant pool, we loaded a volume of the single-stranded fraction after HAP-chromatography equal to a volume of that used for amplification of the same amount of rare cDNA, denatured in the same manner. 300 µl of 6×SSPE (20×SSPE consists of 175.3 gm of NaCl, 27.6 gm of NaH$_2$PO$_4$.H$_2$O, 7.4 gm of EDTA, pH 7.4, per 1 liter) were added to each sample. Blotting was conducted in a Bio-Dot Slot blotting apparatus (Bio-Rad) with Magna Charge Nylon membranes (MSI). Samples of denatured cDNAs were loaded into wells and passive blotting was conducted for 3–5 hours. The membranes were irradiated in a XL-1000 UV crosslinker (Spectronics Corporation) under optimal conditions to immobilize the cDNAs.

Southern hybridization. The immobilized cDNAs were prehybridizated in 5 ml of prehybridization solution (6×SSPE, 1% SDS, 100 µg/ml of salmon sperm DNA denatured at 96° C. for 10 min, 5× Denhardt's solution) at 65° C. for 1 hour. Labeled probes were hybridized to the immobilized cDNAs in 5 ml of hybridization solution (6×SSPE, 1% SDS, 5×Denhardt's solution) at 65° C. overnight, the membranes were washed twice in 100 ml of 2×SSPE, 1% SDS at 65° C. for 30 min, and radioautography was conducted with XRP-5 Kodak film at −80° C. for 1–48 hours to generate the images in FIGS. 5 and 6.

To better quantify hybridization signals, the membranes were exposed to a BAS-III™ screen (Fuji Photo Film Co., Ltd) at room temperature for 2–6 hours, and the signals were analyzed with a BAS 1000 Bio Imaging Analyzer (Fuji Photo Film Co., Ltd). Signals resulting from the presence of single-stranded cDNAs remaining from the abundant cDNA pool were subtracted from signals originating from rare cDNAs.

Generation and analysis of rare cDNA library from *C. elegans* dauer larvae. To generate a rare cDNA library, single-stranded circles from a subtractive hybridization were first introduced directly into *E. coli* strain DH5α by electroporation. To increase the efficiency of transformation, the single-stranded circles were converted into double-stranded circles by random primer synthesis (Feinberg and Vogelstein, 1983) using 1 mm deoxynucleotides. In both cases the electroporated cells were plated on LB agar containing IPTG, X-Gal, and 100 µg/ml ampicillin. Fourteen white colonies produced by electroporation of single-stranded circles and 6 white colonies produced by electroporation of double-stranded circles were inoculated into 3 ml of LB broth with 50 µg/ml ampicillin and grown at 37° C. overnight. Remcombinant plasmids were prepared using the PE Applied Biosystems miniprep kit. The twenty clones were sequenced using the M13 reverse primer (Table 1). To test changes in concentration of these clones, they were digested with EcoRI and loaded onto a 1% agarose gel. After gel electrophoresis, cDNA fragments were eluted using a QIAEX II™ Gel Extraction Kit (QIAGEN). The eluted cDNAs were labeled with [α-$^{32}$P]dCTP as described above.

Figure 7A:
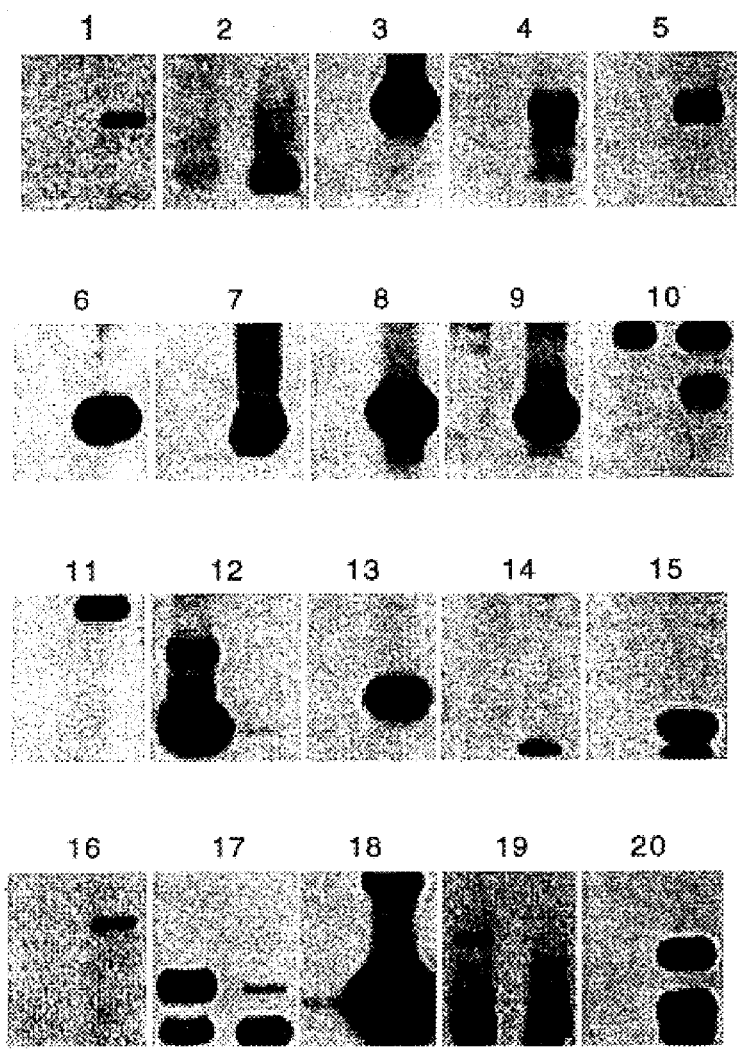
FIGS. 7A–7B.
Figure 7B:
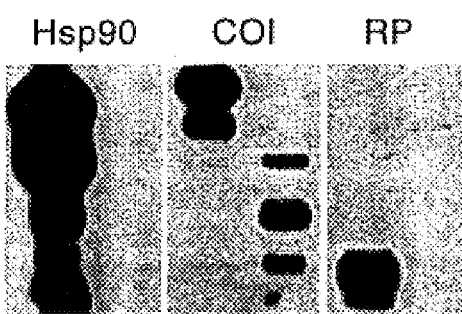

Rare cDNAs in double-stranded pBluescript were prepared by extraction of plasmid DNA from 80,000 recombinant clones. Unnormalized and rare cDNA inserts were obtained by digesting recombinant plasmids with EcoRI. The digests (each containing 200 ng of cDNA inserts) were run on a 1% agarose gel, transferred onto nylon membranes (MSI) and hybridized with each of the 20 clones from the rare cDNA library as recommended by MSI (FIG. 7A). Three abundant probes were used to test changes in concentration of abundant sequences: (1) Hsp 90 was described above, (2) a nearly full-length cDNA of cytochrome c oxidase subunit I (COI) was amplified by PCR from recombinant lambda gt11 DNA, and (3) a partial cDNA of *C. elegans* gene E04A4.8 (Wilson et al. 1994) was obtained from the unnormalized lambda ZapII™ cDNA library. The abundant probes were labeled as described above and hybridized with the unnormalized and rare cDNAs (FIG. 7B). Signals were quantified as described above.

TABLE 1

Identification of 20 clones from "rare" cDNA library prepared by method 2.

| Clone | Gene[1] | SAGE tags[2] | | ESTs[3] | Concentration change (x unnormalized) |
| | | Dauer larvae | Non-dauer stages | | |
| --- | --- | --- | --- | --- | --- |
| 1 | SODA4-1 | 25 | 5 | 0 | 9 |
| 2 | BO495.9 | 7 | 8 | 0 | see text |
| 3 | F18E2.4 | 0 | 0 | 0 | 61 |
| 4 | T20G5.4 | 0 | 0 | 0 | see text |
| 5 | C42C1.9 | 0 | 0 | 0 | 10 |
| 6 | Y37H2B.1 | 0 | 0 | 0 | 55 |
| 7 | T23G11.4 | 0 | 0 | 0 | 26 |
| 8 | F16H6.10 | 0 | 0 | 0 | 100 |
| 9 | F16H6.10 | 0 | 0 | 0 | 100 |
| 10 | Y54E10A.10 | 0 | 0 | 3 | see text |
| 11 | not predicted | | | 1 | 15 |
| 12 | R13.1 | 19 | 3 | 8 | see text |
| 13 | T06G6.3 | 0 | 0 | 2 | 29 |
| 14 | F58B3.6 | 0 | 0 | 2 | 9 |
| 15 | LIR-2B | 0 | 0 | 0 | see text |
| 16 | R09G11.2 | 0 | 0 | 4 | 6 |
| 17 | F19B6.1b | 0 | 0 | 7 | see text |
| 18 | ncl-1 | 8 | 6 | 7 | see text |
| 19 | Y116A8A.9 | 0 | 0 | 7 | see text |
| 20 | K10D3.4 | 4 | 1 | 16 | see text |

[1]Gene name assigned by C. elegans Genome Sequencing Consortium (http://genome.wust1.edu/gsc/C_elegans/elegans shtml and http://www.sanger.ac.uk/Projects/C_elegans/) or by the Caenorhabditis Genetics Center (gopher://elegans.cbs.umn.edu:70/1).
[2]Sequence tags generated by Serial Analysis of Gene Expression (SAGE). The number of tags corresponds to the relative abundance of the mRNA in RNA preparations from dauer larvae and from mixed-stages (unpublished).
[3]ESTs identified by C. elegans genome sequencing project (http://alpha.crbm.cnrs-mop.fr).

EXPERIMENTAL RESULTS AND DISCUSSION

ESTs are invaluable for identifying and annotating genes even when the genomic sequence is already available. Accelerating the discovery of new genes may greatly expedite the identification and cloning human disease genes. Unfortunately, identifying rare transcripts is a very difficult task. The problem of detecting transcripts of genes expressed at low levels is illustrated by the genome and EST sequencing projects for the animal model *C. elegans*, which has only 19,000 genes predicted from the complete genomic sequence of $10^8$ base pairs. Although 118,000 ESTs have been contributed to the *C. elegans* EST database (Thierry-Mieg et al, 1999), these account for only for about half of the predicted genes. The problem of detecting rare transcripts from *C. elegans* can be illustrated by the fact that the existing normalized cDNA libraries are now yielding only one clone corresponding to a new gene in every 20 that are sequenced.

The present invention provides a technology that will greatly facilitate the generation of cDNA libraries enriched in clones representing rare mRNAs. cDNA inserts from *C. elegans* dauer larvae were cloned into the EcoRI site of two phage vectors, lambda gt11 and lambda ZapII™ (FIG. 1). The libraries were constructed in a way to avoid ligation of different cDNAs to each other. Multiple inserts with rare and abundant cDNAs would be lost in the reassociation step, because they would form partial duplexes with the abundant sequences. As a consequence, the background of vectors without inserts was 65% nonrecombinants for the lambda gt11 cDNA library and 45% nonrecombinants for the lambda ZapII™ library. Primers specific for each vector were used to amplify the cDNA inserts.

As rare transcripts are underrepresented even in normalized cDNA libraries (Marra et al., 1998), we decided to subtract abundant cDNAs from unnormalized cDNAs with the help of an abundant cDNA pool. Using a model system, we previously showed that such pools could be generated using a kinetic approach (Il'ichev et al., 1991). Abundant DNAs will reassociate much faster than rare ones and after partial reassociation double-stranded and single-stranded DNAs can be separated. In a similar approach, Bonaldo et al. (1996) used hydroxyapatite chromatography to separate partial DNA/RNA duplexes from single-stranded circles and excess RNA (Bonaldo et al., U.S. Pat. No. 5,846,721). In contrast, we used a simpler method of S1 nuclease digestion to generate an abundant cDNA pool.

After amplification of the cDNA inserts by PCR, they contained common primer sequences and vector sequences adjacent to the cloning site. Because of the very high molar concentration of primer sequences hybridization could occur between them during partial reassociation of cDNA inserts, and correct reassociation of complementary inserts might be very much depressed. Hence, we removed the common sequences by EcoRI digestion (FIG. 2). Double-stranded cDNAs deprived of the common sequences were then denatured and partially reassociated. We used S1 nuclease treatment to eliminate the remaining unreassociated cDNAs. We developed two methods to increase representation of cDNAs corresponding to rare mRNAs. The first method used an excess of an abundant cDNA pool (amplified from the lambda ZapII™ library) to subtract abundant sequences from unnormalized single-stranded cDNAs (amplified 5-fold from the lambda gt11 library). Unreassociated single-stranded cDNAs ("rare" cDNAs) were separated from reassociated hybrids by hydroxyapatite chromatography, and cDNAs having primer sequences from lambda gt11 were then amplified by PCR. Comparative analysis of unnormalized and amplified "rare cDNAs" with 5 probes from C. elegans is presented in FIG. 5 and FIG. 6.

Figure 5:
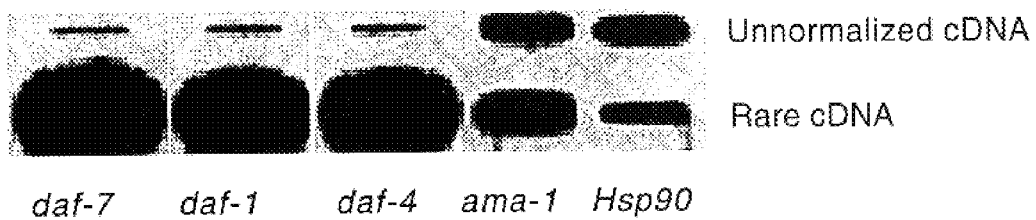
FIG. 5: Hydridization of five probes to unnormalized cDNAs and amplified rare cDNAs (prepared by method 1) from C. elegans dauer larvae. 40 ng of single-stranded unnormalized cDNAs were mixed with 8 μg of abundant cDNAs in 2 μl of 0.3 M sodium phosphate. The mixture was denatured and partially reassociated for 30 min. After HAP-chromatography, single-stranded cDNAs with primer sequences were amplified by PCR. Equal amounts of unnormalized and rare cDNAs were immobilized on a nylon membrane and hybridized with cDNA probes from genes with different levels of the mRNA expression. The concentrations of the five sequences in unnormalized cDNA were estimated by slot blot hybridization of the probes with known amounts of the corresponding unlabeled sequences along side a known amount of unnormalized cDNA.
Figure 6:
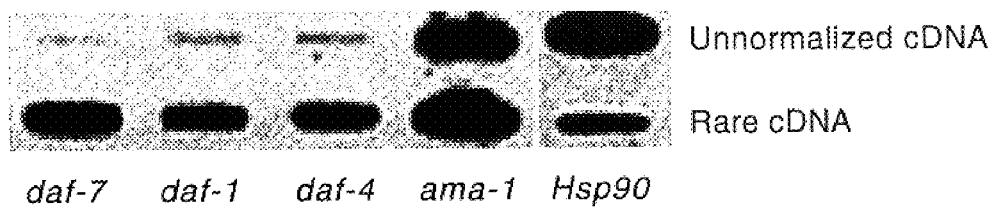
FIG. 6: Hybridization of five probes to amplified unnormalized cDNAs and amplified rare cDNAs (prepared by method 1) from C. elegans dauer larvae, but with greater depletion of abundant cDNAs than shown in FIG. 5. 50 ng of single-stranded unnormalized cDNA were mixed with 5 μg of abundant cDNAs in a volume of 7 μl of 0.3 M sodium phosphate. The mixture was denatured and partially reassociated for 5 min. Then, another 5 μg of denatured abundant cDNAs were added in a volume of 5 μl of water. 2 M sodium phosphate was added to a final concentration 0.3 M and partial reassociation was continued for 5 min. This step was repeated two more times, except that the last partial reassociation was continued for 15 min. After HAP-chromatography, single-stranded cDNAs with primer sequences were amplified by PCR. Equal amounts of unnormalized and rare cDNAs were immobilized on a nylon membrane and hybridized with cDNA probes from genes with different levels of the mRNA expression.

The single-stranded fraction from HAP chromatography contains unreassociated cDNAs from the abundant cDNA pool (FIG. 3) that may produce background hybridization with the probes. Therefore, an aliquot of this fraction corresponding to the amount of such cDNAs in the amplified "rare" cDNA was immobilized on the filter, and we subtracted the corresponding hybridization signals (of the abundant cDNA pool origin) from the hybridization signals of "rare" cDNAs. The results show a remarkable increase of representation of "rare" cDNAs: 94-fold for daf-7, 56-fold for daf-1 and 39-fold for daf-4 (FIG. 5). The concentration of ama-1 (a middle abundant cDNA) increased by 2-fold, and the concentration the abundant Hsp90 cDNA decreased by 3-fold. Hybridization results from greater depletion of abundant cDNAs (by greater reassociation of single strands from the unnormalized library with the abundant cDNAs) are presented in FIG. 6. In this subtraction, the daf sequences were sufficiently abundant not to be enriched as much as in the former subtraction: 6-fold increase for daf-7, 3-fold for daf-1 and daf-4. The abundant Hsp90 cDNA decreased in concentration by 34-fold. The middle-abundant ama-1 cDNA did not change in concentration under these conditions of subtraction.

Gel electrophoretic analysis of cDNA inserts of clones from the amplified "rare" cDNA showed a large decrease in average size relative to the average size of cDNA inserts in the unnormalized library (a reduction from 910 bp to 300 bp). Such a reduction could be explained by destruction of cDNAs during denaturation, partial reassociation or HAP-chromatography. However, we found that the product size was still reduced in experiments adding single-stranded target cDNA that did not pass through these steps to the single-stranded fraction from HAP chromatography as a template for PCR amplification. This reduction was not observed unless the single-stranded HAP fraction was present. Thus, the reduction in size of PCR products does not appear to result from template degradation, but rather because of some component of the single-stranded HAP fraction. Nevertheless, the "rare" cDNA inserts prepared in method 1 can be used for purposes that do not require full-length cDNA clones.

We developed method 2 (FIG. 4) to overcome the problem of reduced cDNA size. It used an excess of an abundant cDNA pool prepared from the lambda gt11 library to subtract abundant cDNAs from unnormalized, single-stranded recombinant circles prepared from the lambda ZapII™ library. The average size of cDNA inserts in 20 random clones from the "rare" cDNA library prepared by method 2 was 800 bp, whereas the average size of cDNA inserts in the unnormalized ZapII™ cDNA library was 950 bp. This size reduction is much less than in method 1, so method 2 is more desirable if longer cDNA clones are required. Sequence analysis of the 20 clones showed that nine of them represent predicted genes not confirmed by any ESTs found in the C. elegans EST project (Table 1). One clone represents a gene not predicted from genomic sequence. Ten clones represent predicted or known genes with matching ESTs (Table 1). Taking into consideration that the normalized cDNA libraries used thus far for the C. elegans EST sequencing project are now yielding few additional expressed genes, libraries produced by method 2 may be valuable for this and other EST sequencing projects. It is also potentially useful for making cDNA libraries representing rare and middle abundant mRNA to study differential expression of regulatory genes by doing subtractions between "rare" cDNA libraries prepared from different developmental stages, different tissues, or from mutant and wild-type strains.

The large fraction of new ESTs in our "rare" cDNA library (Table 1) may result not only from effective removal of abundant sequences, but also may reflect the fact that our library was derived from the dauer stage, whereas the C. elegans EST sequencing project has used embryonic and mixed-stage libraries. A more direct comparison with our dauer-specific library is the Serial Analysis of Gene Expression (SAGE) recently completed on the dauer stage (Table 1). 30,000 unique dauer cDNA tags have been found, and the number of times each tag was represented in the dauer SAGE library has been determined. The most abundantly expressed gene in the dauer stage was represented by more than 4,300 SAGE tags, and 2,300 different genes were represented by five or more tags. Hence, genes with few or no SAGE tags are expressed at relatively low levels. All but one of the clones in the "rare" cDNA library are of this type (Table 1). These two clones (SOD4-1 and R13.1) represent genes that are apparently upregulated in dauer larvae relative to non-dauer stages. Hence, the dauer-specific SAGE data confirm that the "rare" cDNA library consists predominantly of cDNAs representing genes expressed at low levels.

Direct evidence that our "rare" cDNA library is, indeed, enriched in clones representing rare mRNAs came from hybridizations of the 20 clones with unnormalized and "rare" cDNA (FIG. 7A). Hybridization to multiple bands occurs when the clone has internal EcoRI sites, or when the library contains recombinant inserts of different sizes. Hybridization to one band indicates the presence of one or more EcoRI fragments of similar size in the cDNA library. Fifteen of the 20 clones gave little or no signal when hybridized with cDNA inserts from the unnormalized dauer library, but gave strong signals when hybridized with cDNA inserts from the subtracted library. To estimate the ratio in concentrations of the cDNA in the subtracted cDNA library relative to the unnormalized library, this signal was divided by the signal or background present in the corresponding area of the unnormalized lane. Hence, the calculated ratio is an underestimate in cases where little or no signal was detected in the unnormalized library.

Twelve clones hybridized primarily to a single band in the subtracted cDNA preparation (FIG. 7A). The concentrations of these clones increased by factors of 6 to 100 (Table 1). Clone 2 hybridized to four bands in the subtracted cDNA with the most intense signal increased 3-fold. Clone 4 hybridized to three bands in the subtracted cDNA with the most intense signal increased 5-fold. Clone 15 hybridized with two bands 400–500 bp in size with concentrations increased by 20- and 48-fold, and clone 20 hybridized to three bands with concentrations increased by 17-, 21- and 22-fold. The most prominent signal from the subtracted library was obtained from clone 18, which hybridized to two bands. The smaller band also was faintly detected in the unnormalized cDNA. Owing to the signal from unnormalized cDNA, the estimated 197-fold increase in concentration of clone 18 sequences is among the most accurate.

Four clones produced hybridization signals with unnormalized cDNA and do not represent rare mRNAs. Clone 12 hybridized with 3 bands in unnormalized cDNAs with the smallest band giving the strongest signal. This latter signal is the only one detectable in rare cDNA, with a 117-fold decreased intensity. Clones 10 and 17 are more difficult to understand because different clones have different fates after subtraction. Clone 10 revealed one band in unnormalized cDNA and two in rare cDNA. The stronger of the two signals in rare cDNA has the same intensity as its cognate in unnormalized cDNAs. Clone 17 gave two detectable signals in each lane. The larger clone decreased 6-fold in concentration, whereas the smaller one increased slightly in concentration. Clone 19 hybridized to at least three bands in unnormalized cDNA. At least one band decreased in the subtracted library whereas another increased by about 2-fold. It is possible that the different bands represent related sequences with differing kinetics of cross-hybridization, resulting in differential effects on concentration.

FIG. 7B shows the results of hybridizations with abundant sequences obtained from unnormalized cDNA libraries. These showed large decreases in their concentration in the subtracted cDNA. Hsp90, which accounts for approximately 0.3% of total cDNA in unnormalized dauer cDNA (FIG. 5) gave very strong signals in unnormalized cDNAs, but these were not detectable in rare cDNA. Clone RP represents a *C. elegans* gene with similarity to genes encoding the L18AE family of ribosomal proteins. This probe detected two bands in unnormalized cDNA which were not detectable in rare cDNA.

The COI probe also gave two strong signals with unnormalized cDNA that were not detectable in rare cDNA. However, three bands of smaller size were detected. The first possibility is that the abundant clones visible in unnormalized cDNA were effectively reduced in concentration, whereas the rare smaller clones (not detected in unnormalized cDNA) increased in concentration as a result of subtraction. Although cross-hybridization should prevent such differential behavior (not only seen for COI, but also for clones 10, 17 and 19), it is possible that the larger, more abundant clones reassociate more stably, so that smaller, rarer clones tend to remain single-stranded. A second possibility is that the smaller clones resulted from degradation of the larger ones during the preparation of the subtracted library. This may seem unlikely since distinct bands were observed, not a smear. However, it is possible that the subtracted library contains only a few clones derived from discrete degradation products.

Two clones, 8 and 9, represent the same gene (F16H6.10), possibly indicating that our rare cDNA library is small (Table 1). However, clones 8 and 9 differ in structure. Clone 9 is a complete or nearly full-length cDNA that contains all of the predicted exons and 5' and 3' UTR sequences. Clone 8 begins 146 bp downstream of clone 9 and lacks most of exon 1, but has a longer 3' UTR. Both clones differ from the exon structure predicted from genomic sequence by the placement of the 5' splice site for intron 3. The predicted exon 3 is 42 bp long followed by a 135 bp intron. The structures of the two cDNAs show a 128 bp exon and a 49 bp intron.

This rare cDNA library is not normalized with roughly equal numbers of all clones. Instead, it is specifically depleted of abundant sequences. Using the Hsp90 signal as a reference (representing approximately 0.3% of the sequences in the unnormalized dauer library), the representation of each of the 20 clones from the subtracted library was estimated based on phosphorimager quantitation (assuming roughly equivalent specific activities among the probes). These estimated concentrations in the subtracted library ranged from 0.0005% to 0.44% of the cDNA population, and averaged 0.05%. Hence, the approximate number of genes represented in the rare library is 2000. This is an underestimate because it is based on the first 20 clones picked. It seems likely that numerous genes are represented by a small portion of the total clones. Clones that were abundant in the unnormalized library became rare in the subtracted library. Among these 20, the rarest clone (clone 12) is present at 0.12% of the most abundant clone (clone 18). Clone 12 is an example of a cDNA that was abundant in the unnormalized library, yet was still found at low concentration in the subtracted library, showing that this library is not completely devoid of previously abundant sequences.

Genomic sequence analysis of humans and model organisms like *C. elegans* has made extensive use of predictive computational analysis to identify genes. However, such methods are imperfect, so experimental identification of genes by sequencing the ends of a large number of cDNA clones (ESTs) has been a parallel effort with genome sequencing (Marra et al., 1998). The best gene-finding programs detect protein-coding exons with 80% accuracy, but are not very useful for identifying 5' and 3' untranslated regions, regulatory sequences or alternative transcripts (Claverie, 1999). In *C. elegans*, comparison of cDNAs with predicted genes shows that only 50% of the encoded proteins are predicted correctly (Claverie, 2000). Errors include added or missed exons, incorrect exon-intron boundaries, and fused genes.

In human DNA, identification of genes by computational methods is more difficult. It has been estimated that more than 30% of exon predictions are over-predictions; that is, they do not overlap any experimental exons. The comparison of computational predictions with the annotated gene structures in the human chromosome 22 sequence showed that only 20% of annotated genes had all exons predicted exactly (Dunham et al., 1999). Sequencing more ESTs has been suggested as the best way to annotate the human genome, but identifying genes expressed at very low levels is currently a very difficult and expensive task. The subtractive methods presented herein potentially can make experimental detection of such genes a practical reality. cDNA libraries enriched for rare sequences will also be of great importance to the analysis of gene expression patterns with DNA microarrays. First, EST-based microarrays currently lack representation of many genes expressed at low levels. Second, use of subtracted libraries for hybridization with microarrays should greatly improve the sensitivity of this method.

The formation of an abundant sequence pool, in which previously abundant species were over-represented and previously rare species were under-represented has been demonstrated in a simple model system of only two sequences (Il'chev et al. 1991). The creation of an abundant cDNA pool and the use of subtractive hybridization to create a cDNA library with increased representation of rare clones has been described (Bonaldo et al. 1996). However, those results were very modest in comparison with the results in this application. A key aspect of this invention is the method to create a high-quality, abundant cDNA pool. This involves novel approaches, including the use of S1 nuclease digestion (rather than HAP-chromatography) for elimination of single-stranded DNA from a mixture of single-stranded and double-stranded molecules. Attempts by Soares et al. (U.S. Pat. No. 5,846,721) to generate a high-quality abundant cDNA pool involved many steps. The method provided herein greatly simplifies the procedure by eliminating steps for in vitro transcription, conversion of RNA into DNA, and HAP-chromatography for preparation of the abundant cDNA pool. The present invention also avoids the use of quenching oligonucleotides to prevent hybridization between common sequences in the vector. Instead, the method of the present invention efficiently removed such common sequences by restriction digestion.

References

| U.S. Pat. No. 5,482,845 | Soares et al. |
| U.S. Pat. No. 5,637,685 | Soares et al. |
| U.S. Pat. No. 5,702,898 | Bonaldo et al. |
| U.S. Pat. No. 5,846,721 | Soares et al. |

Bonaldo, M. F., Lennon, G., and Soares, M. B. (1996). Normalization and subtraction: two approaches to facilitate gene discovery. *Genome Research* 6, 791–806.

Claverie, J. -M. (1999). Computational methods for the identification of differential and coordinated gene expression. *Hum. Mol. Genet.* 8, 1821–1832.

Claverie, J. -M. (2000). Do we need a huge new centre to annotate the human genome? *Nature* 403, 12.

Dunham, I., Shimizu, N., Roe, B. A., Chissoe, S., et al. The DNA sequence of human chromosome 22. *Nature* 402, 489–495.

Feinberg, A. P. and Vogelstein, B. (1983). A technique for radiolabeling DNA restriction endonuclease fragments to high specific activity. *Anal. Biochem.* 132, 6–13.

Il'ichev, A. A., Kishchenko, G. P., Petrenko, V. A., and Puzyrev, A. T. (1991). Method for equalizing contents of sequences with different copy number in heterogeneous DNA mixture. *Mol. Biol. Engl. Tr.* 25, 1068–1076.

Ko, M. S. H. (1990). An equalized cDNA library by reassociation of short double-stranded cDNAs. *Nucleic Acids Res.* 18, 5705–5711.

Kohara, Y., the Kohara Lab and Collaborators. (1999). Post genomics strategies and resources in *C. elegans*. In *Abstracts of the 12th International C. elegans Meeting* (Madison), p.4.

Lewin, B., (1994) Genes V (Oxford, New York), 674–676.

Marra, M. A., Hiller, L., & Waterston, R. H. (1998). Expressed sequence tags—ESTablishing bridges between genomes. *Trends Genet.* 14, 4–7.

Patanjali, S. R., Parimoo, S. & Weissman, S. M. (1991). Construction of a uniform-abundance (normalized) cDNA library. *Proc. Natl. Acad. Sci. USA* 88, 1943–1947.

Puzyrev, A. T., Chroniary K., & Moschonas, N. K. (1995). Normalized cDNA library from human erythroleukemia cells. *Mol. Biol. Engl. Tr.* 29, 58–61.

Puzyrev, A. T., Il'ichev, A. A., Petrenko, V. A. (1990). A method for equalizating concentrations of dsDNAs in a mixture. In *Abstracts of the 1 st Conference on Human Genome* (Moscow), pp.91–92, in Russian.

Sasaki, Y. F., Ayusawa, D., & Oishi, M. (1994). Construction of a normalized cDNA library by introduction of a semi-solid mRNA-cDNA hybridization system. *Nucleic Acids Res.* 22, 987–992.

Soares, M. B., Bonaldo, M. F., Jelene, P., Su, L., Lawton, L., & Efstratiadis, A. (1994). Construction and characterization of a normalized cDNA library. *Proc. Natl. Acad. Sci. USA* 91, 9228–9232.

The *C. elegans* Sequencing Consortium (1998). Genome Sequence of the Nematode *C. elegans*: A Platform for Investigating Biology. *Science* 282, 2012–2018.

Thierry-Mieg, J., Thierry-Mieg, D., Shin-i, T., and Kohara, Y. (1999). Expressed genes in *C. elegans*. In *Abstracts of the 12th International C. elegans Meeting* (Madison), p.3.

Wilson, R., Ainscough, R., Anderson, K., Baynes, C. et al. (1994). 2.2 MB of coutiguous nucleotide sequence from chromosome III of *C. elegans*. *Nature* 368, 32–38.

What is claimed is:

1. A method for producing a cDNA library enriched for rare cDNAs and reduced in abundant cDNAs which comprises:
   (a) obtaining a pool of linear double-stranded cDNAs;
   (b) cloning a first portion of the pool of cDNAs into a first vector to create a first cDNA library;
   (c) cloning a second portion of the pool of cDNAs into a second vector to create a second cDNA library;
   (d) producing single-stranded linear cDNA inserts (target cDNA) from the first cDNA library;
   (e) producing single-stranded circles (target cDNA) from the second cDNA library;
   (f) producing a pool of abundant linear cDNAs (driver cDNA) from the first and the second DNA libraries by the following steps:
   (i) amplifying the cDNA inserts from the first and the second libraries by polymerase chain reaction using two pairs of appropriate primers which specifically hybridize with the first and second vectors, respectively;
   (ii) removing DNA sequences common to all of the amplified products from step (i);
   (iii) denaturing the amplified products from step (ii);
   (iv) partially reassociating the denatured products from step (iii) in a hybridization mixture under appropriate hybridization conditions so as to produce duplexes of abundant cDNAs, and
   (v) removing unreassociated cDNAs from step (iv), thereby producing the pools of abundant linear cDNAs from the first and the second cDNA libraries;
   (g) hybridizing the linear cDNA inserts from step (d) or the single-stranded circles from step (e) with an excess amount of the abundant cDNA pool produced from the second cDNA library or the first cDNA library, respectively, from step (v) under hybridization conditions to produce duplexes, and (h) isolating single-stranded linear cDNA inserts or single-stranded circles which remain after the hybridization of step (g), thereby producing cDNA or a cDNA library enriched for rare cDNAs and reduced in abundant cDNAs.

2. The method of claim 1, wherein removing common sequences in step (f) (ii) is performed by restriction enzyme digestion of the amplified products.

3. The method of claim 1, wherein isolating the reassociated abundant cDNA duplexes of step (f) (v) is performed by treating the hybridization mixtures of step (f) (iv) with S1 nuclease so as to degrade any single-stranded cDNAs.

4. The method of claim 1, wherein isolating unreassociated linear cDNAs or single-stranded circles from reassociated cDNA duplexes of step (g) is performed by subjecting the hybridization mixtures to hydroxyapatite column chromatography so as to separate single-stranded cDNAs or single-stranded circles from DNA duplexes.

5. The method of claim 1, wherein the pool of linear double-stranded cDNAs of step (a) comprises cDNAs produced by reverse transcriptase using mRNA isolated from a biological sample.

6. The method of claim 5, wherein the biological sample is a human biological sample or a non-human biological sample.

7. The method of claim 6, wherein the human biological sample is a tissue sample, a blood sample, a saliva sample, an embryonic sample or a tumor biopsy.

8. The method of claim 6, wherein the non-human biological sample is an embryonic sample, a tissue sample, an animal sample or a plant sample.

9. The method of claim 1, wherein the first vector or the second vector is a phage vector, a phagemid vector, a retroviral vector or a plasmid vector.

10. The method of claim 1, wherein the first vector is a lambda gt11 phage vector.

11. The method of claim 1, wherein the second vector is a lambda ZapII™ vector.

12. The method of claim 1, further comprising:

(a) amplifying the single-stranded linear cDNA inserts in step (h) by polymerase chain reaction using primers specific for the first vector, so as to thereby produce cDNA enriched for rare cDNAs and reduced in abundant cDNAs;

(b) electroporating single-stranded circles in step (h) into host cells or converting single-stranded circles in step (h) into double-stranded circles and electroporating them into host cells, so as to thereby produce a cDNA library enriched for rare cDNAs and reduced in abundant cDNAs.

13. The method of claim 1, wherein the hybridization conditions to produce duplexes of step (g) comprise 0.3 M sodium phosphate (pH 7.0) and cDNA concentrations and reassociation reaction times to obtain $C_o t$s from 20 to 380.

14. The method of claim 1, wherein the first vector is lambda gt11 and the two primer pairs used for polymerase chain reaction have the following sequences:

(a) 5'-CTCCTGGAGCCCGTCAGTAT-3' (SEQ ID NO:1) and 5'-GTAATGGTAGCGACCGGCGC-3' (SEQ ID NO:2); and (b) 5'-GGAGCCCGTCAGTATCGGCG-3' (SEQ ID NO:3) and 5'-GTAGCGACCGGCGCTCAGCT-3' (SEQ ID NO:4).

15. The method of claim 1, wherein the second vector is lambda ZapII™ and the primers used for polymerase chain reaction have the following sequences:

5'-TCGAGGTCGACGGTATCGAT-3' (SEQ ID NO:5) and

5'-CCGCTCTAGAACTAGTGGATC-3' (SEQ ID NO:6).

* * * * *